United States Patent [19]
Weinstein et al.

[11] Patent Number: 5,166,390
[45] Date of Patent: Nov. 24, 1992

[54] S-SUBSTITUTED CARBONYL SUBSTITUTED BETA-THIOACRYLAMIDE BIOCIDES AND FUNGICIDES

[75] Inventors: Barry Weinstein, Dresher, Pa.; Philip Robinson, Isle of Palms, S.C.; Katherine E. Flynn, Fairfield, Ohio; Cherylann Schieber, Narberth, Pa.

[73] Assignee: Rohm and Haas Company, Philadelphia, Pa.

[21] Appl. No.: 461,553

[22] Filed: Jan. 5, 1990

[51] Int. Cl.$^5$ ............... C07C 327/00; C07C 303/00; C07C 321/00; A61K 31/21
[52] U.S. Cl. .................... 558/254; 564/39; 564/162; 514/513; 514/545
[58] Field of Search ................. 558/254; 564/39, 162; 514/513, 545

[56] References Cited

U.S. PATENT DOCUMENTS 3,914,301 10/1975 Miller et al. ............... 558/254
4,021,482 5/1977 Schempp ............... 558/254
4,198,304 4/1980 Inoue et al. ............... 558/254

OTHER PUBLICATIONS

Isothiazole Chemistry-IX Selectivity in Carbanion Attack on N-Ethyl-3-Isothiazolone, W. D. Crow and I. Gosney, (1968).
Isothiazole Chemistry VL Reactions of Carbanions with N-Ethyl-3-Isothiazolone, W. D. Crow and I. Gosney, Aust. J. Chem., 1969, 22, 765-74.
Aoyagi (CA 102 78589) (1985).

Primary Examiner—Mary C. Lee
Assistant Examiner—Robert C. Whittenbaugh
Attorney, Agent, or Firm—Terry B. Morris

[57] ABSTRACT

A compound of the formula

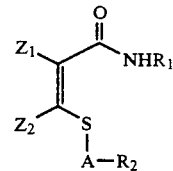

wherein
$R_1$ is an organic radical having at least 2 carbon atoms;
$R_2$ is an organic radical; and
$A = CO, CH_2$, or $CHR_3$ where $R_3$ is unsubstituted or substituted alkyl; and
$Z_1$ and $Z_2$ are independently selected from hydrogen, halogen, and $(C_1-C_4)$alkyl
and use as a fungicide and biocide.

2 Claims, No Drawings

S-SUBSTITUTED CARBONYL SUBSTITUTED BETA-THIOACRYLAMIDE BIOCIDES AND FUNGICIDES

BACKGROUND OF THE INVENTION

1. Field of the Invention

This invention relates to biocides and fungicides.

2. Description of the Prior Art

The following references were considered pertinent, but do not describe or suggest the present invention: Miller, et al., U.S. Pat. No. 3,914,301 (Oct. 21, 1975), commonly assigned; W. D. Crow and I. Gosney, Aust. J. Chem., 22, 765-774 (1969); W. D. Crow and I. Gosney, Tetradedron, 26, 1463-1473(1970).

SUMMARY OF THE INVENTION

There is a need for alternative biocides and fungicides, especially improved ones.

It is therefore an object of the present invention to provide novel compounds which are useful in any locus subject to contamination by bacteria or fungi.

These objects and others as will become apparent from the following detailed description, are achieved by the present invention which in one aspect comprises a compound of the formula

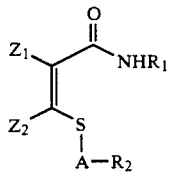

wherein $R_1$ is an organic radical having at least 2 carbon atoms;

$R_2$ is an organic radical;

$A = CO, CH_2,$ or $CHR_3$ where $R_3$ is unsubstituted or substituted alkyl; and $Z_1$ and $Z_2$ are independently selected from hydrogen, halogen, and $(C_1-C_4)$alkyl.

In another aspect the invention comprises the use of such a compound as a biocide or as a fungicide, and compositions comprising such compounds in fungicidally effective amount and in an agronomically acceptably carrier. In another aspect the invention comprises a method of controlling or inhibiting growth of bacteria in a locus comprising incorporating into or onto the locus a biocidally effective amount of the compound.

DETAILED DESCRIPTION OF THE INVENTION AND THE PREFERRED EMBODIMENTS

The novel compounds of the invention have been found to be useful as bactericides or as fungicides or both. The compounds of the invention have the formula

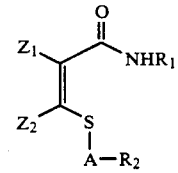

wherein $R_1$ is an organic radical having at least 2 carbon atoms;

$R_2$ is an organic radical;

A is carbonyl (CO), methylene or alkyl substituted methylene wherein the alkyl substituent may be substituted or unsubstituted.

$Z_1$ and $Z_2$ are independently selected from hydrogen, halogen, and $(C_1-C_4)$ alkyl.

In a preferred embodiment $R_1$ and $R_2$ are independently selected from optionally substituted $(C_2-C_{12})$ alkyl, $(C_2-C_{12})$ alkenyl, $(C_2-C_{12})$ alkynyl, $(C_3-C_{12})$ cycloalkyl, $(C_6-C_{10})$ aryl, aryl $(C_1-C_8)$ alkyl, aryl $(C_2-C_8)$ alkenyl, aryl $(C_2-C_8)$ alkynyl, heteroyl, heteroyl $(C_1-C_8)$ alkyl, heteroyl $(C_2-C_8)$ alkenyl; wherein the substituent may be one or more cyano, thiocyano, isothiocyano, halogen, $(C_1-C_6)$ alkyl, halo $(C_1-C_6)$ alkyl, $(C_1-C_6)$ alkoxy, halo $(C_1-C_6)$ alkoxy, nitro, carboxy, carbo $(C_1-C_6)$ alkoxy, $(C_1-C_6)$ aryloxy, hydroxy or amino groups; and heteroyl is selected from pyridyl, quinolyl, isoquinolyl, triazolyl, furyl, thiopheneyl, benzothiopheneyl, pyrrolidinyl, pyrrolyl, indolyl, ferrocenyl, and pyranyl; and A is carbonyl, methylene, or hydroxyalkylmethylene; and $Z_1$ and $Z_2$ are hydrogen.

In a more preferred embodiment, $R^1$ is $(C_4-C_{12})$ alkyl or $(C_6-C_{12})$ cycloalkyl;

$R_2$ is $(C_2-C_6)$ alkyl optionally substituted by one or more amino, carboxy, carbomethoxy, phenoxy or halo groups, $(C_2-C_6)$ alkenyl optionally substituted with one or more halo or carbo $(C_1-C_6)$ alkoxy groups, phenyl optionally substituted with one or more $(C_1-C_6)$ alkoxy, halo $(C_1-C_6)$ alkyl, polyhalo $(C_1-C_6)$ alkyl, halo or nitro groups, or a heteroyl group selected from optionally substituted furyl, thiopheneyl or pyridinyl wherein the substituents are independently selected from halogen, nitro or $(C_1-C_6)$ alkyl groups; and A is carbonyl; and $Z_1$ and $Z_2$ are hydrogen.

Still more preferably the compounds are those wherein $R_1$ is $(C_5-C_{12})$ alkyl or alkynyl. Also preferred are those wherein $R_1$ is selected from the group consisting of 2,4,4-trimethyl-2-pentyl; or propargyl; A is CO, $R_2$ is selected from the group consisting of substituted or unsubstituted aryl, heteroyl, alkyl, alkenyl, alkynyl, aralkyl, alkoxy, ferrocenyl, cycloalkyl, cycloalkenyl, and

wherein $Y_1$ and $Y_2$ are aryl, alkyl, or together make a ring.

Most preferred compounds are those wherein $R_1$ is selected from the group consisting of n-$C_8H_{17}$, 2,4,4-trimethyl-2-pentyl and propargyl; $R_2$ is selected from the group consisting of ethyl, phenyl, 2-chloroethyl, 3-methoxy-4-nitrophenyl, diphenylamino, 4-butylphenyl, and 3,5-chlorophenyl; and $Z_1$ and $Z_2$ are H.

The term "halo" by itself or as a part of another substituent means chloro, fluoro, bromo and iodo. The term "alkyl" by itself or as a part of another substituent, unless otherwise stated, means straight and branched chain groups such as methyl, ethyl, propyl, butyl, pentyl, hexyl, heptyl, octyl, nonyl, decyl, undecyl, dodecyl, and the like. The term "haloalkyl" by itself or as a part of another substituent is an alkyl group of the stated number of carbon atoms having one or more halo atoms bonded thereto such as chloromethyl, bromoethyl, trifluoromethyl, bromodifluoromethyl, and the like.

The term "cycloalkyl" by itself or as a part of another substituent, unless otherwise stated, means carbocyclic structures such as cyclopropyl, cyclobutyl, cyclopentyl, cyclohexyl, cycloheptyl, cyclooctyl, cyclonoryl, cyclodecyl, cyclomendecyl, cyclolodecyl, and the like. The term alkenyl means straight and branched chain groups containing at least one carbon to carbon double bond such as propylene, butylene, pentene, hexene, heptene, octene, nonene, decene, undeene, dodecene, and the like.

The term alkynyl means straight and branched chain groups containing at least one carbon to carbon tripple bond such as propargyl, butynyl, pentynyl, hexynyl, heptynyl, octynyl, nonynyl, decynyl, undecynyl, dodecynyl and the like.

The term "pesticidally or fungicidally effective amount" means a quantity of compound with causes a statistically significant reduction of the pest or fungi or bacteria population as compared to a control group.

The beta-thioacrylamides of the invention can be used in any locus subject to contamination by bacteria or fungi. Typical loci subject to contamination by bacteria are in aqueous systems such as water cooling, laundry wash water, oil/water systems such as cutting oils, oil fields and the like where microorganisms need to be killed or where their growth needs to be controlled.

Specific loci for bacteriostatic application include disinfectants, sanitizers, cleaners, deodorizers, liquid and powder soaps, skin removers, oil and grease removers, food processing chemicals, dairy chemicals, food preservatives, animal food preservatives, paint, lazures, stains, hospital and medical antiseptics, metal working fluids, cooling water, air washers, petroleum production, paper treatment, paper mill slimicides, petroleum products, adhesives, textiles, pigment slurries, latexes, leather and hide treatment, petroleum fuel, jet fuel, laundry sanitizers, agricultural formulations, inks, mining, nonwoven fabrics, petroleum storage, rubber, sugar processing, tobacco, swimming pools, cosmetics, toiletries, pharmaceuticals, chemical toilets, household laundry products, diesel fuel additives, waxes and polishes and other applications where water and organic materials come in contact under conditions which allows the growth of undesired microorganisms. Solutions of beta-thioacrylamides can also applied to a solid substrate, such as fabric, leather, or wood, as a preservative, or admixed with plastics. It is known in the art that the performance of biocides can frequently be enhanced by combination with one or more other biocides. In fact, there have been numerous examples of synergistic combinations of biocides. Thus, other known biocides may be combined advantageously with the beta-thioacrylamides of this invention.

See Industrial Antimicrobial Agents Encyclopedia of Chemical Technology, Volume 13, for a list of suitable other biocides. More specific industries and applications for the compounds are:

| Industry | Application |
|---|---|
| Adhesives, Sealants | Adhesives |
| | caulks |
| | sealants |
| agriculture/food chain | adjuvant preservation |
| | agricultural active ingredient |
| | agricultural chemical preservative |
| | agricultural formulations preservation |
| | animal feed preservation |
| | dairy chemicals |
| | fertilizer preservation |
| | food processing chemicals |
| | grain preservation |
| | post-harvest produce protection |
| | sugar processing |
| | tobacco |
| Construction products | asphalt/concrete |
| | cement modifiers |
| | construction products |
| | roof mastics |
| | synthetic stucco |
| | wall mastics |
| | joint cement |
| Cosmetics and toiletries | cosmetics |
| | raw materials for cosmetics, toiletries |
| | toiletries |
| Disinfectants, antiseptics | antiseptic |
| | disinfectant |
| Emulsions, dispersions | aqueous dispersions |
| | dispersed pigments |
| | latex |
| | photographic emulsions |
| | pigment slurries |
| | polymer latices |
| formulated household products | fabric softeners |
| | polishes |
| | waxes |
| | hand dish detergents |
| | raw materials |
| | liquid detergents |
| | hand soaps |
| Industrial processing, misc | electrodeposition paint, baths, rinses. |
| | electrodeposition pre-treatment, post rinses |
| | Industrial fluids preservation |
| | pasteurization baths |
| | process aid preservation |
| Industrial water treatment | air washers |
| | cooling towers |
| | cooling water |
| | water cooling |
| | preservation/treatment of wooden cooling tower slats and structural members |
| | can warmers |
| | brewery pasteurization |
| | closed loop water cooling systems |
| Laundry | household laundry products |
| | laundered goods |
| | laundry wash water |
| | sanitizers-laundry |
| Leather, Leather products | leather and hide |
| | leather and hide products |
| Lubricants, hydraulic aids | automotive lubricants and fluids |
| | conveyor lubricants |
| | greases |
| | hydraulic fluids |
| | lubricants |
| Medical devices | diagnostic enzymes |
| | diagnostic kits |
| | medical devices |
| metalworking & related app's | cutting fluids |
| | Metal cleaning |
| | metalworking fluids |

| Industry | Application |
|---|---|
| Odor control (active ingredient) | air conditioning animal bedding cat litter chemical toilet prep'ns deodorizers humidifiers industrial deodorants sanitary formulations toilet bowls |
| Paints and coatings coating | emulsions paints |
| Paper and wood pulp, their products | absorbant materials of paper and wood pulp packaging materials of paper and wood pulp paper paper products paper treatment soap wrap wood pulp wood pulp products |
| paper mill | paper mill slimicides pulp and paper slurries |
| Petroleum refining, fuels | aviation fuels (jet fuel, aviation gas) crude oils burner, diesel and turbine fuel oils coal slurries diesel fuel additives diesel fuels fuels gasoline heating oils hydrocarbons Kerosene liquefied petroleum gas petrochemical feedstocks petroleum products, storage, transportation and production recycled petroleum products residual fuel oils turbine oils |
| Photographic Chemicals and process | Photographic processing - wash water, rinses photoprocessing Photoplate processing chemicals (developers, stabilizers etc) |
| Printing | Fountain solutions (printing) Ink components (pigments, resins, solvents, etc) Inks |
| Sanitizers (active) | sanitizers sanitizers-dairy sanitizers-dental sanitizers-fermentation sanitizers-food preparation sanitizers-food processing sanitizers-medical sanitizers-rendering sanitizers-veterinary |
| Soaps, detergents, cleaners | cleaners detergents household cleaners industrial cleaners liquid soaps oil and grease remover powdered soaps raw materials for cleaning products soaps surfactants |
| Textiles, textile products | bonded fabrics burlap canvas canvas goods carpet backing carpets clothing coated fabrics curtains draperies engineering textiles fibers |
| | geotextiles goods made of textiles knitted fabrics nets nonwoven fabrics rope rugs textile accessories textile products textiles upholstery woven fabrics yarn |
| Textile processing | dye fixatives dyes fiber lubricants hand modifiers sizes Textile processing fluids |
| Therapeutic (active or preservative) | animal health/veterinary aquaculture dental human health pharmaceutical/therapeutic |
| water purification | charcoal beds deionization resins filters membranes reverse osmosis membranes ultrafilters Water purification water purification pipes, tubing |
| wood applications | lazures (wood stains) wood wood products |
| Miscellaneous | alcohols bedding incorporating water or gels ceramic contact lens cases-leaching electronic circuitry electronics chemicals enzymes-food production enzymes enzymes-industrial gel cushions marine antifoulants mildewcides wood plastics laundry mining natural rubber latex oil field injection waters including enhanced recover injection fluids, drilling, fracturing and completion fluids pipes plastics polymer systems polymers and resins (synthetic and natural) reagent preservation rubber rubber products skin remover solid protective/decorative films stains swimming pools waste treatment water beds |

The compounds of this invention are useful in the preventative and curative treatment of phytopathogenic fungi, i.e., useful applied either before or after the plant's exposure to a fungus. They are effective against a broad spectrum of fungi, including those of the phycomycetes, ascomycetes, basidiomycetes and deuteromycetes classes. They are particularly effective against rusts, tomato late blight and rice blast. Consequently, various compounds of this invention may be useful in treating fungi which may affect cereal crops, fruit crops and vegetable crops.

The beta-thioacrylamide compounds of the invention can be applied as fungicidal sprays by methods commonly employed, such as conventional high-gallonage hydraulic sprays, low-gallonage sprays, airblast, aerial sprays and dusts. The dilution and rate of application will depend upon the type of equipment employed, the method and frequency of application desired and diseases to be controlled, but the effective amount for application is usually from about 5 grams (gm) to about 22 kilograms (kg), preferably from about 0.010 to about 1.0 kg per hectare.

As a seed protectant, the amount of fungicide coated on the seed is usually at a dosage rate of about 0.0001 to about 10 grams (gm) and preferably from about 0.1 to about 10 gm per 1 kilogram of seed. As a soil fungicide the beta-thioacrylamides can be incorporated in the soil or applied to the surface usually at a rate of 0.01 to about 22 kg, preferably about 0.05 to about 11 kg and more preferably from about 0.1 to about 3.3 kg per hectare. As a foliar fungicide the beta-thioacrylamides can be applied at a rate of from about 0.01 to about 11 kg, preferably from about 0.02 to about 5.5 kg and more preferably from about 0.1 to about 3.3 kg per hectare.

The present invention is useful for the control of fungi and can be utilized at various loci such as the seed, the soil or the foliage. For such purposes these compounds can be used in the technical or pure form as prepared, as solutions or as formulations. The compounds are usually taken up in a carrier or are formulated so as to render them suitable for subsequent dissemination as fungicides. For example, these beta-thioacrylamides can be formulated as wettable powders, emulsifiable concentrates, dusts, granular formulations, aerosols, or flowable emulsion concentrates. In such formulations, the beta-thioacrylamides are extended with a liquid or solid carrier and, when desired, suitable surfactants are incorporated.

It is usually desirable, particularly in the case of foliar spray formulations, to include adjuvants, such as wetting agents, spreading agents, dispersing agents, stickers, adhesives and the like in accordance with agricultural practices. Such adjuvants commonly used in the art can be found in *McCutcheon's Emulsifiers and Detergents, McCutcheon's Emulsifiers and Detergents/Functional Materials* and *McCutcheon's Functional Materials* all published annually by McCutcheon Division of MC Publishing Company (New Jersey). In general, the beta-thioacrylamides of this invention can be dissolved in appropriate solvents such as acetone, methanol, ethanol, dimethylformamide or dimethyl sulfoxide and such solutions extended with water. The concentrations of the solution can vary from 1% to 90% with a preferred range being 5 to 50% (weight percentage). For the preparation of emulsifiable concentrates, the beta-thioacrylamides can be dissolved in suitable organic solvents or a mixture of solvents, together with an emulsifying agent which permits dispersion of the fungicide in water. The concentration of the active ingredient in emulsifiable concentrates is usually 10% to 90% and in flowable emulsion concentrates, this can be as high as 75% (weight percent). Water based flowable formulations of the beta-thioacrylamides can be prepared with a concentration of active ingredients in the range of 5 to 70% by weight, preferably 20 to 50% by weight.

A typical flowable formulation is prepared by wet-milling a mixture of 35 parts of beta-thioacrylamides, 10 parts of Barden clay, 4 parts of sodium lignosulfonate, 1 part of an anionic wetting agent and 50 parts of water.

Wettable powders suitable for spraying can be prepared by admixing the beta-thioacrylamide compound with a finely divided solid, such as clays, inorganic silicates and carbonates, and silicas and incorporating wetting agents, sticking agents, and/or dispersing agents in such mixtures. The concentration of active ingredients in such formulations is usually in the range of 5% to 98%, preferably 40% to 75% (weight percent) obtained by blending 50 parts of an active ingredient selected from the S-substituted carbonyl substituted beta-thioacrylamides of Examples 1–120, 45 parts of a synthetic precipitated hydrated silicon dioxide sold under the trademark Hi-Sil, 1 part of an anionic naphthalenic sulfonate wetting agent and 4 parts of sodium lignosulfonate (Marasperse N-22). In another preparation of a kaolin type (Barden) clay is used in place of the Hi-Sil in the above wettable powder and in another such preparation 25% of the Hi-Sil is replaced with a synthetic sodium silico aluminate sold under the trademark Zeolex 7. Dusts are prepared by mixing the amides and salts and complexes thereof with finely divided inert solids which can be organic or inorganic in nature. Materials useful for this purpose include botanical flours, silicas, silicates, carbonates, talc and clays. One convenient method of preparing a dust is to dilute a wettable powder with a finely divided carrier. Dust concentrates containing 20% to 80% (weight percent) of the active ingredient are commonly made and are subsequently diluted to 1% to 10% use concentration.

The compounds of the present invention may also be utilized in combination with other fungicides such as:

(a) dithiocarbamates and derivatives such as: ferric dimethyldithiocarbamate (ferbam), zinc dimethyldithiocarbamate (ziram), manganese ethylenebisdithiocarbamate (maneb) and its coordination product with zinc ion (mancozeb), zinc ethylenebisdithiocarbamate (zineb), zinc propylenebisdithiocarbamate (propineb), sodium methyldithiocarbamate (metham), tetramethylthiuram disulfide (thiram), the complex of zineb and polyethylene thiuram disulfide, 3,5-dimethyl-1,3,5-2H-tetrahydrothiadiazine-2-thione (dazomet); and mixtures of these and mixtures with copper salts;

(b) nitrophenol derivatives such as: dinitro-(1-methylheptyl) phenyl crotonate (dinocap), 2-sec-butyl-4,6-dinitrophenyl-3,3-dimethylacrylate (binapacryl), and 2-sec-butyl-4,6-dinitrophenyl isopropyl carbonate;

(c) heterocyclic structures such as: Systhane (a registered trademark of Rohm and Haas for myclobutanil), triademifon, N-trichloromethylthiotetrahydrophthalimide (captan), N-trichloromethylthiophthalimide (folpet), 2-heptadecyl-2-imidazole acetate (glyodine), 2-octylisothiazolone-3, 2,4-dichloro-6-(o-chloroanilino)-s-triazine, diethyl phthalimidophosphorothioate, 4-butyl-1,2,4-triazole, 5-amino-1-[bis(dimethylamino)phosphinyl]-3-phenyl-1,2,4-triazole, 5-ethoxy-3-trichloromethyl-1,2,4-thiadiazole, 2,3-dicyano-1,4-dithiaanthraquinone (dithianon), 1,3-dithiolo-[4,5-b]quinoxaline-2-thione (thioquinox), methyl 1-(butylcarbamoyl)-2-benzimidazole carbamate (benomyl), 2-4'-(thiazolyl) benzimidazole (thiabendazole), 4-(2-chlorophenylhydrazono)-3-methyl-5-isoxazolone, 3-(3,5-dichlorophenyl)-5-ethenyl-5-methyl-2,4-oxazolidinedione (vinclozolin), 3-(3,5-dichlorophenyl)-N-(1-methylethyl)-2,4-di-alphaoxo-1-imidazolinecarboxamide (dichlorophenyl)-1,2-dimethylcyclopropane-1,2-dicarboximide (procymidone), beta-(4-chlorophenoxy)-alpha-(1,1-dimethylethyl)-1H-1,2,4-triazole-1-ethanol (triadimenol), 1-(4-chlorophenoxy)-3,3-dimethyl-1-(1H-1,2,4-triazol-1-yl)-2-butanone (triadimefon), beta-[(1,1'-biphenyl)-4-yloxy]-alpha-(1,1-dimethylethyl)-1H-1,2,4-triazole-1-ethanol (bitertanol), 2,3-dichloro-N-(4-fluorophenyl)maleimide (fluoroimide), 1-[2-(2,4-dichlorophenyl)-4-propyl-1,3-dioxolan-2-yl-methyl]-1H-1,2,4-triazole, pyridine-2-thiol-1-oxide, 8-hydroxyquinoline sulfate and metal salts thereof, 2,3-dihydro-5-carboxanilido-6-methyl-1,4-oxathiin-4,4-dioxide, 2,3-dihydro-5-carboxanilido-6-methyl-1,4-oxathiin,alpha-(phenyl)-alpha-(2,14-dichlorophenyl)-5-pyrimidinyl-methanol (triarimol), cis-N-[(1,1,2,2-tetrachloroethyl)-thio]-4-cyclohexene-1,2-dicarboximide, 3-[2-(3,5-dimethyl-2-oxycyclohexyl)-2-hydroxy]-glutarimide (cycloheximide), dehydroacetic acid, N-(1,1,2,2-tetrachloroethylthio)-3a,4,7,7a-tetrahydrophthalimide (captafol), 5-butyl-2-ethylamino-4-hydroxy-6-methylpyrimidine (ethirimol), acetate of 4-cyclodecyl-2,6-dimethylmorpholine (dodemorph), and 6-methyl-2-oxo-1,3-dithiolo[4,5-b]-quinoxaline (quinomethionate);

(d) miscellaneous halogenated fungicides such as: tetrachloro-p-benzoquinone (chloranil), 2-3-dichloro-1,4-naphthoquinone (dichlone), 1,4-dichloro-2,5-dimethoxybenzene (chlorneb), 3,5,6-trichloro-o-anisic acid (tricamba), 2,4,5,6-tetrachloroisophthalonitril (TCPN), 2,6-dichloro-4-nitroaniline (dichloran), 2-chloro-1-nitropropane, polychloronitrobenzenes such as: pentachloronitrobenzene (PCNB) and tetrafluorodichloroacetone;

(e) fungicidal antibiotics such as: griseofulvin, kasugamycin and streptomycin;

(f) copper-based fungicides such as: copper hydroxide, cuprous oxide, basic cupric chloride, basic copper carbonate, copper terphthalate, copper naphthenate and Bordeaux mixture; and (g) miscellaneous fungicides such as: diphenyl, sultone, dodecylguanidine acetate (dodine), phenylmercuric acetate, N-ethylmercuri-1,2,3,6-tetrahydro-3,6-endomethano-3,4,5,6,7,7-hexachlorophthalimide, phenyl-mercuric monoethanol ammonium lactate, p-dimethylaminobenzene sodium sulfonate, methyl isothiocyanate, 1-thiocyano-2,4-dinitrobenzene, 1-phenylthiosemicarbazide, nickel-containing compounds, calcium cyanamide, lime sulfur, 1,2-bis(3-methoxycarbonyl-2-thioureido) benzene (thiophanate-methyl).

Many of the novel S-substituted beta-thioacrylamides of the invention can be prepared by preparing a compound of the formula

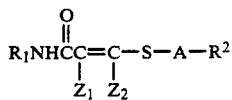

wherein $R_1$, $R_2$, A, $Z_1$ and $Z_2$ are as defined herein above, comprising:

A. reducing a compound of the formula

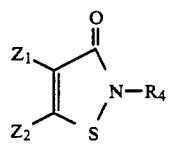

with a reducing means so as to form an anion as represented by the following equation:

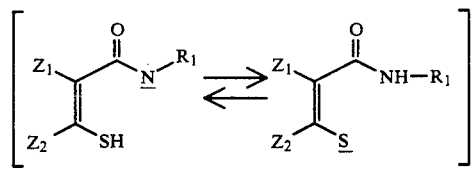

B. quenching said anion with an A-$R_2$-supplying electrophile such as an acid chloride, activated alkyl halide, carbonyl chloride, or an epoxide.

Examples 3, 9, 10, 12, 13, 40, 53, 54, 63 and 68 provide detailed descriptions of the above reaction.

Suitable Y-supplying electrophiles are propionyl chloride, methacryloyl chloride, 2,6-dichlorobenzoyl chloride, 3-(chloromethyl)benzoyl chloride, heptanoyl chloride, 3-chloropropionyl chloride, pivaloyl chloride, phenoxyacetyl chloride, 2-ethylhexanoyl chloride, 2,4,6-trifluorobenzoyl chloride, 4-chlorobutyryl chloride, methyl oxalyl chloride, chloroacetyl chloride, 1-pyrrolidinecarbonyl chloride, 4-(trifluoromethyl)benzyl bromide, ethyl bromoacetate, 2-(chloromethyl)-benzoyl chloride, 3-bromobenzoyl chloride, dichloroacetyl chloride, methyl D,L-propionate, diphenylcarbamyl chloride, 2,4-dimethylbenzoyl chloride, 3-chloropivaloyl chloride, 4-heptoxybenzoyl chloride, 4-nitrobenzoyl chloride, 4-isothiocyanobenzoyl chloride, cyclopropionyl chloride, 3-methyl-2-thiophenecarbonyl chloride, 3-carbomethoxypropionyl chloride, ethyl succinyl chloride, 5-bromo-2-pyridinecarbonyl chloride, 2-naphthoyl chloride, hydrocinnamoyl chloride, acryloyl chloride, methyl 4-(chloroformyl)butyrate, styrylacetyl chloride, 3,4-dihydro-2,2-dimethyl-4-oxo-2H-pyran-6-carbonyl chloride, phenylpropiolyl chloride, 2-octenoyl chloride, 2-cyclopentene-1-acetyl chloride, cyclohexylacetyl chloride, 4-quinolinecarbonyl chloride, 4-nitrocinnamoyl chloride, 3,5-dinitrobenzoyl chloride, 2-nitro-3-methoxybenzoyl chloride, 2-methyl-4-nitrobenzoyl chloride, 2,4-dichlorobenzoyl chloride, 1,4-dihydro-2-methylbenzoyl chloride, 2,3-dichlorobenzoyl chloride, 3,4-dichlorobenzoyl chloride, 3-nitro-4-chlorobenzoyl chloride, 3-methoxy-4-nitrobenzoyl chloride, 4-methylbenzoyl chloride, 2,5-dinitrobenzoyl chloride, 4-chloro-3-pyridinecarbonyl chloride, methyl 7-(chloroformyl)heptanoate, 5-bromofuroyl chloride, 3,4-dinitrobenzoyl chloride, methyl 8-(chloroformyl)octanoate, methyl 5-(chloroformyl)pentanoate, methyl 9-(chloroformyl)nonanoate, 4-phenoxybutyryl chloride, 5-phenylpenta-2,4-dienoyl chloride, 4-butylbenzoyl chloride, phenylacetyl chloride, cinnamyl bromide, cinnamoyl chloride, 4-methoxybenzoyl chloride, 5-nitro-2-furoyl chloride, 2,5-dichloro-3-thiophenecarbonyl chloride, benzo(6)thiophene-2-carbonyl chloride, furylacrylic acid*, trans-4-(trifluoromethyl)cinnamic acid*, 1,2,3,4-tetrahydro-2-naphthanoic acid*, methoxyacetic acid*, 3,5-dichlorobenzoic acid*, nicotinic acid*, fumaric acid, monomethyl ester*, 11-cyanoundecanoic acid*, 2,4-hexadienoic acid*, ethoxyacetic acid*, 1-methyl-2-pyrrolecarboxylic acid*, vinylacetic acid*, 3-furoic acid*, 4-vinylbenzoic acid*, 3-thiophenecarboxylic acid*, 3-(2-thienyl)acrylic acid*, 3-carboxyphenylisothiocyanate*, pinonic acid*, quinaldic acid*, indole-3-carboxylic acid*, 3-phenylbutyric acid*, 3-phenoxypropionic acid*, 4-phenylbutyric acid*, ferrocenecarboxylic acid*, 2-phenylcinnamic acid*, 4-pentenoic acid*, trans-2-pentenoic acid*, 2-octynoic acid*, 1,2-epoxy-3-phenoxypropane, 2,3-epoxypropyl 4-methoxyphenyl ether, 2-(epoxyethyl)furan, 4-fluorobenzoyl chloride, cyclohexanecarbonyl chloride, 2-bromobenzoyl chloride, benzoyl chloride, 1-cyclohexenecarbonyl chloride, ethylmalonyl chloride, 2-chloropyridine-3-carbonyl chloride, N-chloromethyltriazole, 3-anisoyl chloride, 3-cyclopentylpropionyl chloride, 2-furoyl chloride. (* The acid chloride corresponding to these acids is made in situ as described using either diphenylphosphinic chloride, phenyldichlorophosphate, or diethyl chlorophosphate.)

A reducing means is herein defined as any reducing agent capable of reducing the carbon-sulfur bond of a 4-isothiazoline-3-one to form an amonic structure. Examples of suitable reducing agents are lithium aluminum hydride, lithium triethyl borohydride, and the like.

Another method of producing the compounds of this invention is to react a propioic acid or propiolic amide with a suitable mercaptan compound. If a propioic acid is used in the above reaction, the propiolic acid sulfide formed thereby is further converted to the corresponding amide, the compound of this invention. Examples 47, 90 and 113 provide detailed descriptions of this method of synthesis.

The following examples will further illustrate this invention, but are not intended to limit it in any way.

The following compounds are examples of this invention.

1. N-octyl-cis-3-(benzoylthio)acrylamide
2. N-octyl-cis-3-(ethylmalonylthio)acrylamide
3. N-octyl-cis-3-[(4-fluorobenzoyl)thio]acrylamide
4. N-octyl-cis-3-(cyclohexanecarbonylthio)acrylamide
5. N-octyl-cis-3-[(2-bromobenzoyl)thio]acrylamide
6. N-octyl-cis-3-[3-(2-chloropyridine)carbonylthio]acrylamide
7. N-octyl-cis-3-[1-(1,2,4-triazoyl)methylthio]acrylamide
8. N-octyl-cis-3-[(3-methoxybenzoyl)thio]acrylamide
9. N-octyl-cis-3-[(1-cyclohexene)carbonylthio]acrylamide
10. N-octyl-cis-3-(propanoylthio)acrylamide
11. N-octyl-cis-3-[(3-cyclopentanepropanoyl)thio]acrylamide
12. N-octyl-cis-3-(phenylacetylthio)acrylamide
13. N-octyl-cis-3-[(trans-3-phenylprop-2-ene)thio]acrylamide
14. N-octyl-cis-3-[(trans-3-phenylprop-2-enoyl)thio]acrylamide
15. N-octyl-cis-3-(2-furoylthio)acrylamide
16. N-octyl-cis-3-[(4-methoxybenzoly)thio]acrylamide
17. N-octyl-cis-3-[(5-nitro-2-furoyl)thio]acrylamide
18. N-octyl-cis-3-[(2,5-dichloro-3-thiophene)carbonylthio]acrylamide
19. N-octyl-cis-3-[(2-benzo(6)thiophene)carbonylthio]acrylamide
20. N-octyl-cis-3-[(2-butenoyl)thio]acrylamide
21. N-octyl-cis-3-[(2,6-dichlorobenzoyl)thio]acrylamide
22. N-octyl-cis-3-[(3-(chloromethyl)benzoyl)thio]acrylamide
23. N-octyl-cis-3-(octanoylthio)acrylamide
24. N-octyl-cis-3-[(3-chloropropanoyl)thio]acrylamide
25. N-octyl-cis-3-[(1,1-dimethylpropanoyl)thio]acrylamide
26. N-octyl-cis-3-(phenoxyacetylthio)acrylamide
27. N-octyl-cis-3-[(2-ethylhexanoyl)thio]acrylamide
28. N-octyl-cis-3-[2,4,6-trifluorobenzoyl)thio]acrylamide
29. N-octyl-cis-3-[(4-chlorobutanoyl)thio]acrylamide
30. N-octyl-cis-3-(methyloxalylthio)acrylamide
31. N-octyl-cis-3-(chloroacetylthio)acrylamide
32. N-octyl-cis-3-[(1-pyrrolidine)carbonylthio]acrylamide
33. N-octyl-cis-3-[(4-(trifluoromethyl)benzyl)thio]acrylamide
34. N-octyl-cis-3-(ethoxycarbonylmethanethio)acrylamide
35. N-octyl-cis-3-[(2-(chloromethyl)benzoyl)thio]acrylamide
36. N-octyl-cis-3-[(3-bromobenzoyl)thio]acrylamide
37. N-octyl-cis-3-(dichloroacetylthio)acrylamide
38. N-octyl-cis-3-[(2-methoxycarbonylethane)thio]acrylamide
39. N-octyl-cis-3-[(1-hydroxy-3-(4-methoxyphenoxy)-2-propane)thio]acrylamide
40. N-octyl-cis-3-[(1-hydroxy-3-phenoxy-2-propane)thio]acrylamide
41. N-octyl-cis-3-(diphenylaminocarbonylthio)acrylamide
42. N-octyl-cis-3-[(2-furan)-2-hydroxyethane)thio]acrylamide
43. N-octyl-cis-3-[(2,4-dimethylbenzoyl)thio]acrylamide
44. N-octyl-cis-3-[(2,2-dimethyl-3-chloropropanoyl)thio]acrylamide
45. N-octyl-cis-3[(4-heptoxybenzoyl)thio]acrylamide
46. N-octyl-cis-3-[(4-nitrobenzoyl)thio]acrylamide
47. N-octyl-cis-3-[(2-amino-2-carboxyethane)thio]acrylamide
48. N-octyl-cis-3-[(4-isothiocyanobenzoyl)thio]acrylamide
49. N-octyl-cis-3-(cyclopropanecarbonylthio)acrylamide
50. N-octyl-cis-3-[(3-methyl-2-thiophene)carbonylthio]acrylamide
51. N-octyl-cis-3-[(3-methoxycarbonylpropanoyl)thio]acrylamide
52. N-octyl-cis-3-[(3-ethoxycarbonylpropanoyl)thio]acrylamide
53. N-octyl-cis-3-[(5-bromo-2-pyridine)carbonylthio]acrylamide
54. N-octyl-cis-3-[(3,5-dichlorobenzoyl)thio]acrylamide
55. N-octyl-cis-3-[(3-pyridine)carbonylthio]acrylamide
56. N-octyl-cis-3-[(2-naphthanoyl)thio]acrylamide
57. N-octyl-cis-3-[(trans-3-ethoxycarbonyl-2-propenoyl)thio]acrylamide
58. N-octyl-cis-3-[(11-cyanoundecanoyl)thio]acrylamide
59. N-octyl-cis-3-[(trans,trans-2,4-hexadienoyl)thio]acrylamide
60. N-octyl-cis-3-(ethoxyacetylthio)acrylamide
61. N-octyl-cis-3-[(1-methyl-2-pyrrole)carbonylthio]acrylamide
62. N-octyl-cis-3-(3-furoylthio)acrylamide
63. N-octyl-cis-3-[(3-butenoyl)thio]acrylamide
64. N-octyl-cis-3-[(4-ethenylbenzoyl)thio]acrylamide
65. N-octyl-cis-3-[(3-thiophene)carbonylthio]acrylamide
66. N-octyl-cis-3-[(trans3-(2-thiophene)propenoyl)thio]acrylamide
67. N-octyl-cis-3-[(3-cyanobenzoyl)thio]acrylamide
68. N-octyl-cis-3-[(trans-3-(2-furan)propenoyl)thio]acrylamide
69. N-octyl-cis-3-[(3-phenylpropanoyl)thio]acrylamide 70. N-octyl-cis-3-[(trans-3-(4-(trifluoromethyl)phenyl)propenoyl)thio]acrylamide
71. N-octyl-cis-3-(propenoylthio)acrylamide
72. N-octyl-cis-3-[(3-quinoline)carbonylthio]acrylamide
73. N-octyl-cis-3-[(1-isoquinoline)carbonylthio]acrylamide
74. N-octyl-cis-3-[(1,2,3,4-tetrahydronaphth-2-oyl)thio]acrylamide
75. N-octyl-cis-3-[(2,2-dimethyl-3-acetylcyclobutane)carbonylthio]acrylamide
76. N-octyl-cis-3-[(2-quinoline)carbonylthio]acrylamide
77. N-octyl-cis-3-[(3-indole)carbonylthio]acrylamide
78. N-octyl-cis-3-[(3-phenylbutanoyl)thio]acrylamide
79. N-octyl-cis-3-[(3-phenoxypropanoyl)thio]acrylamide
80. N-octyl-cis-3-[(4-phenylbutanoyl)thio]acrylamide
81. N-octyl-cis-3-(ferrocenecarbonylthio)acrylamide
82. N-octyl-cis-3-[(cis-2,3-diphenylpropenoyl)thio]acrylamide
83. N-octyl-cis-3-[(4-pentenoyl)thio]acrylamide
84. N-octyl-cis-3-[(trans-2-pentenoyl)thio]acrylamide
85. N-octyl-cis-3-[(4-methoxycarbonylbutanoyl)thio]acrylamide
86. N-octyl-cis-3-[(2-octynoyl)thio]acrylamide
87. N-octyl-cis-3-(methoxyacetylthio)acrylamide
88. N-octyl-cis-3-[(4-phenylbut-3-enoyl)thio]acrylamide
89. N-octyl-cis-3-[(3,4-dihydro-2,2-dimethyl-4-oxo-2H-pyran-6-carbonyl)thio]acrylamide
90. N-cyclododecyl-cis-3-(acetylthio)acrylamide
91. N-octyl-cis-3-[(3-phenylpropanoyl)thio]acrylamide
92. N-octyl-cis-3-[(trans-2-octenoyl)thio]acrylamide
93. N-octyl-cis-3-[(3-cyclopentene)acetylthio]acrylamide
94. N-octyl-cis-3-(cyclohexaneacetylthio)acrylamide
95. N-octyl-cis-3-[(4-quinoline)carbonylthio]acrylamide
96. N-octyl-cis-3-[(trans-3-(4-nitrophenyl)propenoyl)thio]acrylamide
97. N-octyl-cis-3-[(3,5-dinitrobenzoyl)thio]acrylamide
98. N-octyl-cis-3-[(2-nitro-3-methoxybenzoyl)thio]acrylamide
99. N-octyl-cis-3-[(2-methyl-4-nitrobenzoyl)thio]acrylamide
100. N-octyl-cis-3-[(2,4-dichlorobenzoyl)thio]acrylamide
101. N-octyl-cis-3-[(2-methylcyclohexa-2,5-diene)carbonylthio]acrylamide
102. N-octyl-cis-3-[(2,3-dichlorobenzoyl)thio]acrylamide
103. N-octyl-cis-3-[(3,4-dichlorobenzoyl)thio]acrylamide
104. N-octyl-cis-3-[(3-nitro-4-chlorobenzoyl)thio]acrylamide
105. N-octyl-cis-3-[(3-methoxy-4-nitrobenzoyl)thio]acrylamide
106. N-octyl-cis-3-[(4-methylbenzoyl)thio]acrylamide
107. N-octyl-cis-3-[(2,5-dinitrobenzoyl)thio]acrylamide
108. N-octyl-cis-3-[(4-chloro-3-pyridine)carbonylthio]acrylamide
109. N-octyl-cis-3-[(trans,trans-5-phenyl-2,4-pentadienoyl)thio]acrylamide
110. N-octyl-cis-3-[(7-methoxycarbonylheptanoyl)thio]acrylamide
111. N-octyl-cis-3-[(5-bromo-2-furoyl)thio]acrylamide
112. N-octyl-cis-3-[(3,4-dinitrobenzoyl)thio]acrylamide
113. N-(2-propynyl)-cis-3-(benzoylthio)acrylamide
114. N-(1,1,4,4-tetramethylbutyl)-cis-3-(benzoylthio)acrylamide
115. N-octyl-cis-3-[(4-butylbenzoyl)thio]acrylamide
116. N-[2-(4-morpholine)ethyl]-cis-3-(benzoylthio)acrylamide
117. N-octyl-cis-3-[(8-methoxycarbonyloctanoyl)thio]acrylamide
118. N-octyl-cis-3-[(5-methoxycarbonylphentanoyl)thio]acrylamide
119. N-octyl-cis-3-[(9-methoxycarbonylnonanoyl)thio]acrylamide
120. N-octyl-cis-3-[(4-phenoxybutanoyl)thio]acrylamide Melting points for appropriate compounds are listed below in Table 1:

TABLE 1

| mp (°C.) | Compound # | Method of Preparation Example # |
|---|---|---|
| 87–91 | 3 | 3 |
| 81–82 | 4 | 3 |
| 93–97 | 7 | 9 |
| 67–71 | 9 | 9 |
| 68–70 | 10 | 10 |
| 108–111 | 13 | 13 |
| 84–87 | 14 | 13 |
| 101–102 | 16 | 13 |
| 128–130 | 17 | 13 |
| 75–77 | 18 | 13 |
| 115–118 | 19 | 13 |
| 91–92 | 21 | 10 |
| 88–90 | 22 | 10 |
| 79–82 | 23 | 10 |
| 45–47 | 25 | 10 |
| 95–99 | 26 | 10 |
| 93–98 | 28 | 10 |
| 73–74 | 29 | 10 |
| 103–105 | 32 | 10 |
| 86–88 | 33 | 10 |
| 78–80 | 36 | 10 |
| 77–80 | 40 | 40 |
| 151–155 | 41 | 10 |
| 99–101 | 43 | 10 |
| 57–59 | 44 | 10 |
| 117–118 | 45 | 10 |
| 105–109 | 46 | 10 |
| 102–104 | 49 | 10 |
| 68–70 | 51 | 10 |
| 59–61 | 52 | 10 |
| 99–102 | 54 | 54 |
| 66–68 | 55 | 54 |
| 96–99 | 56 | 10 |
| 92–95 | 57 | 54 |
| 77–78 | 58 | 54 |
| 104–106 | 59 | 54 |
| 65–69 | 60 | 54 |
| 60–62 | 63 | 63 |
| 103–104 | 65 | 63 |
| 94–98 | 67 | 63 |
| 86–92 | 68 | 68 |
| 56–59 | 69 | 10 |
| 114–118 | 70 | 68 |
| 118–121 | 72 | 68 |
| 81–84 | 74 | 68 |
| 47–52 | 75 | 63 |
| 119–122 | 76 | 63 |
| 125–128 | 77 | 63 |
| 73–77 | 80 | 63 |
| 114–116 | 81 | 63 |
| 89–94 | 82 | 63 |
| 79–81 | 83 | 63 |
| 60–62 | 84 | 63 |
| 107–109 | 88 | 10 |
| 60–63 | 92 | 10 |
| 55–57 | 93 | 10 |
| 61–64 | 94 | 10 |
| 80–86 | 95 | 10 |
| 149–152 | 97 | 10 |
| 98–99 | 98 | 10 |
| 102–105 | 99 | 10 |
| 86–88 | 100 | 10 |
| 56–58 | 102 | 10 |

TABLE 1-continued

| mp (°C.) | Compound # | Method of Preparation Example # |
|---|---|---|
| 116–120 | 104 | 10 |
| 90–93 | 106 | 10 |
| 130–134 | 107 | 10 |
| 100–102 | 108 | 10 |
| 132–134 | 109 | 10 |
| 134–136 | 111 | 10 |
| 108–111 | 112 | 10 |
| 131–134 | 113 | 113 |
| 51–52 | 117 | 10 |
| 72–74 | 118 | 10 |
| 70–71 | 120 | 10 |

EXAMPLE 3

To a stirred slurry of 0.11 g (0.003 mol) of lithium aluminum hydride in 20 ml of anhydrous tetrahydrofuran under nitrogen was added a solution of 2.13 g (0.01 mol) of 2-octyl-4-isothiazolin-3-one in 5 ml of anhydrous tetrahydrofuran dropwise over a 5 min period. After 30 min this solution was used in the following step.

To a stirred solution of 1.59 g (0.01 mol) of 4-fluorobenzoyl chloride in 20 ml of anhydrous tetrahydrofuran under nitrogen was added the solution prepared above in the first step. After 12 h at room temperature the reaction mixture was poured into 10% aqueous hydrochloric acid and was extracted with ethyl acetate. The organic layer was washed with water, saturated aqueous sodium bicarbonate, brine and dried over magnesium sulfate. Filtration and removal of solvents gave a mixture of the cis and trans isomers. Separation by flash column chromatography (Merck 60 ® silica gel, 10% to 25% ethyl acetate/hexane eluant) gave 0.73 g (22% yield) of N-octyl-cis-3-[(4-fluorobenzoyl)thio]acrylamide as a pale yellow solid, m.p. 87°–91° C., as reported in Table 1.

The above procedure was used to make other analogs by the replacement of 4-fluorobenzoyl chloride with one of the following reagents: benzoyl chloride, cyclohexanecarbonyl chloride, and 2-bromobenzoyl chloride, to give compounds of examples 1,4, and 5, respectively.

EXAMPLE 9

To a stirred solution of 1.06 g (0.005 mol) of 2-octyl-4-isothiazolin-3-one in 5 ml of anhydrous tetrahydrofuran was added 5.0 ml (0.005 mol) of a 1.0M solution of lithium triethylborohydride in tetrahydrofuran dropwise over a 5 min period. After 30 min this solution was used in the following step.

To a stirred solution of 0.72 g (0.005 mol) of 1-cyclohexenecarbonyl chloride in 20 ml of anhydrous tetrahydrofuran under nitrogen was added the solution prepared above in the first step. After 12 h at room temperature the reaction mixture was poured into 10% aqueous hydrochloric acid and was extracted with ethyl acetate. The organic layer was washed with water, saturated aqueous sodium bicarbonate, brine and dried over magnesium sulfate. Filtration and removal of solvents gave a mixture of the cis and trans isomers. Separation by flash column chromatography (Merck 60 ® silica gel, 25% ethyl acetate/hexane eluant) gave 0.40 g (25% yield) of N-octyl-cis-3-[(1-cyclohexene)carbonylthio]acrylamide as a white solid, m.p. 67°–71° C., as described in Table 1.

The above procedure was repeated with the replacement of 1-cyclohexenecarbonyl chloride with one of the following: ethylmalonyl chloride, 2-chloropyridine-3-carbonyl chloride, N-chloromethyltriazole, 3-anisoyl chloride, 3-cyclopentylpropionyl chloride, and 2-furoyl chloride to give compoounds of examples 2,6–8, 11, and 15, respectively.

EXAMPLE 10

To a cooled (0° C.), stirred solution of 21.3 g (0.10 mol) of 2-octyl-4-isothiazolin-3-one in 400 ml of anhydrous ethyl ether was added dropwise 30 ml (0.03 mol) of a 1.0M solution of lithium aluminum hydride in tetrahydrofuran over a 20 min period. After the addition the mixture was stirred at 0° C. for 1 hr. Over a 15 min period 8.96 ml (0.10 mol) of propionyl chloride was added. After this addition the mixture was allowed to warm to room temperature. After 12 hr the reaction mixture was a white solid suspended in an orange solution. The mixture was filtered and the filtrate was diluted with 300 ml of ethyl acetate and washed once with 300 ml of 10% aqueous hydrochloric acid. The organic layer was set aside and the aqueous layer was extracted three times with ethyl acetate. The combined organic layers were washed with water until the washes were neutral in pH, washed with brine, and dried over anhydrous magnesium sulfate. Filtration and removal of solvents gave N-octyl-cis-3-(propanoylthio)acrylamide as an oil which crystallized upon standing. These crude crystals were recrystallized from ethyl ether/hexane to give 16 g (59% yield) as white crystals, m.p. 68°–70° C., and is reported in Table 1.

The above procedure was used to make other compounds by replacing propionyl chloride with methacryloyl chloride, 2,6-dichlorobenzoyl chloride, 3-(chloromethyl)benzoyl chloride, heptanoyl chloride, 3-chloropropionyl chloride, pivaloyl chloride, phenoxyacetyl chloride, 2-ethylhexanoyl chloride, 2,4,6-trifluorobenzoyl chloride, 4-chlorobutyryl chloride, methyl oxalyl chloride, chloroacetyl chloride, 1-pyrrolidinecarbonyl chloride, 4-(trifluoromethyl)benzyl bromide, ethyl bromoacetate, 2-(chloromethyl)benzoyl chloride, 3-bromobenzoyl chloride, dichloroacetyl chloride, methyl D,L-propionate, diphenylcarbamyl chloride, 2,4-dimethylbenzoyl chloride, 3-chloropivaloyl chloride, 4-heptoxybenzoyl chloride, 4-nitrobenzoyl chloride, 4-isothiocyanobenzoyl chloride, cyclopropionyl chloride, 3-methyl-2-thiphenecarbonyl chloride, 3-carbomethoxypropionyl chloride, ethyl succinyl chloride, 5-bromo-2-pyridinecarbonyl chloride, 2-naphthoyl chloride, hydrocinnamoyl chloride, acryloyl chloride, methyl 4-(chloroformyl)butyrate, styrylacetyl chloride, 3,4-dihydro-2,2-dimethyl-4-oxo-2H-pyran-6-carbonyl chloride, phenylpropiolyl chloride, 2-octenoyl chloride, 2-cyclopentene-1-acetyl chloride, cyclohexylacetyl chloride, 4-quinolinecarbonyl chloride, 4-nitrocinnamoyl chloride, 3,5-dinitrobenzoyl chloride, 2-nitro-3-methoxybenzoyl chloride, 2-methyl-4-nitrobenzoyl chloride, 2,4-dichlorobenzoyl chloride, 1,4-dihydro-2-methylbenzoyl chloride, 2,3-dichlorobenzoyl chloride, 3,4-dichlorobenzoyl chloride, 3-nitro-4-chlorobenzoyl chloride, 3-methoxy-4-nitrobenzoyl chloride, 4-methylbenzoyl chloride, 2,5-dinitrobenzoyl chloride, 4-chloro-3-pyridinecarbonyl chloride, 5-pheylpenta-2,4-dienoyl chloride, methyl 7-(chloroformyl)heptanoate, 5-bromofuroyl chloride, 3,4-dinitrobenzoyl chloride, 4-butylbenzoyl chloride, methyl 8-(chloroformyl)octanoate, methyl 5-(chloroformyl)pentanoate, methyl 9-(chloroformyl)nonanoate, and 4-phenoxybutyryl chloride, to give the compounds of examples 20-38, 41, 43-46, 48-52, 56, 69, 71, 85, 88, 89, 91-112, 115 and 117-120, respectively.

EXAMPLE 12

To a cooled (−78° C.), stirred solution of 2.0 g (0.0094 mol) of 2-octyl-4-isothiazolin-3-one in 50 ml of anhydrous tetrahydrofuran under nitrogen was added dropwise 2.82 ml (0.0028 mol) of a 1.0M solution of lithium aluminum hydride in tetrahydrofuran over a 20 min. period. After the addition the mixture was stirred at −78° C. for 1 hr. Over a 15 min period 1.24 ml (0.0094 mol) of phenylacetyl chloride was added. After this addition the mixture was allowed to warm to room temperature. After 12 hr the reaction mixture was a white solid suspended in an orange solution. The mixture was filtered and the filtrate was diluted with ethyl acetate and washed once with aqueous saturated sodium bicarbonate solution. The organic layer was set aside and the aqueous layer was extracted three times with ethyl acetate. The combined organic layers were washed once with water, with brine, and dried over anhydrous magnesium sulfate. Filtration and removal of solvents gave N-octyl-cis-3-(phenylacetylthio)acrylamide as an oil which crystallized upon standing to give 3.0 g (96% yield) of a white solid whose NMR is reported in Table 2.

EXAMPLE 13

To a stirred solution of 2.0 g (0.0094 mol) of 2-octyl-4-isothiazolin-3-one in 100 ml of anhydrous tetrahydrofuran under nitrogen was added dropwise at room temperature 2.8 ml of a 1.0M solution of lithium aluminum hydride in tetrahydrofuran. The mixture was stirred for 15 min and then 1.85 g (0.0094 mol) of cinnamyl bromide was added. After 12 h the mixture was poured into 10% aqueous hydrochloric acid which resulted in the immediate precipitation of the product as a white solid. The solid was collected by suction-filtration, washed several times with water, and air-dried to give 1.5 g (48% yield) of N-octyl-cis-3-[(trans-3-phenylprop-2-ene)thio]acrylamide as a white, fluffy solid, m.p. 108°–111° C., and is reported in Table 1.

The above procedure was used to make other compounds by substituting one of the following for cinnamyl bromide: cinnamoyl chloride, 4-methoxybenzoyl chloride, 5-nitro-2-furoyl chloride, 2,5-dichloro-3-thiophenecarbonyl chloride, and benzo(6)thiophene-2-carbonyl chloride to give the compounds of examples 14 and 16-19, respectively.

EXAMPLE 40

To a cooled (0° C.), stirred solution of 2.13 g (0.010 mol) of 2-octyl-4-isothiazolin-3-one in 40 ml of anhydrous tetrahydrofuran under nitrogen was added dropwise 3.0 ML (0.003 mol) of a 1.0M solution of lithium aluminum hydride in tetrahydrofuran over a 20 min period. After the addition the mixture was stirred at 0° C. for 1 hr. Over a 15 min period a solution of 1.5 g (0.01 mol) of 1,2-epoxy-3-phenoxypropane in 5 ml of tetrahydrofuran was added. After this addition the mixture was allowed to warm to room temperature. After 12 hr the reaction mixture was diluted with ethyl acetate and washed once with aqueous saturated sodium bicarbonate solution. The organic layer was set aside and the aqueous layer was extracted three times with ethyl acetate. The combined organic layers were washed once with water, with brine, and dried over anhydrous magnesium sulfate. Filtration and removal of solvents gave 2.8 g (80% yield) of N-octyl-cis-3-[(1-hydroxy-3-phenoxy-2-propane)thio]acrylamide as a pale yellow solid, m.p. 77°–80° C., as reported in Table 1.

The above procedure was repeated with the substitution of one of the following epoxides for the 1,2-epoxy-3-phenoxypropane: 2,3-epoxypropyl-4-methoxyphenyl ether or 2-(epoxyethyl)furan to give compounds of examples 39 and 42, respectively.

EXAMPLE 47

To a stirred, cooled (−30° C.) solution of 18.42 g (0.143 mol) of n-octylamine in 25 ml of aqueous methanol was added 10 g (0.119 mol) of methyl propiolate dropwise. After the addition the reaction mixture was allowed to warm to room temperature and stir for 12 h. The reaction mixture was poured into ice-cold 10% aqueous hydrochloric acid and extracted with dichloromethane. The combined organic layers were washed with saturated aqueous sodium bicarbonate, brine, and dried over magnesium sulfate. Filtration and removal of solvents gave a crude mixture which was purified by column chromatography (Merck 60 ® silica gel, 25% ethyl acetate/hexane eluant) to give N-octylpropiolamide.

To a stirred solution of 1.0 g (0.0083 mol) of L-cysteine in 10 ml of absolute ethanol was added 8.09 g (0.025 mol) of a 21 wt % solution of sodium ethoxide in absolute ethanol. The reaction mixture was stirred for 30 min and then cooled to 0° C. To the mixture was added a solution of 1.5 g (0.0083 mol) of N-octylpropiolamide in 10 ml of absolute ethanol. After 1 h the mixture was diluted with ethanol and water and filtered. The filtrate was acidified with 10% aqueous hydrochloric acid and extracted with dichloromethane. The organic layer was washed with saturated aqueous sodium bicarbonate, water, and brine. Removal of solvents gave 0.37 g (15% yield) of N-octyl-cis-3-[(2-amino-2-carboxyethane)thio]acrylamide as a white powder whose NMR is reported in Table 2.

EXAMPLE 54

To a cooled (0° C.), stirred solution of 0.85 g (0.004 mol) of 2-octyl-4-isothiazolin-3-one in 20 ml of anhydrous tetrahydrofuran under nitrogen was added 1.19 ml (0.0012 mol) of a 1.0M solution of lithium aluminum hydride in tetrahydrofuran. The mixture was stirred at 0° C. for 20 min and then used in the next step as described below.

To a stirred, cooled (0° C.) slurry of 0.048 g (0.002 mol) of hexane-washed sodium hydride in 5 ml of anhydrous dimethoxyethane under nitrogen was added dropwise a solution of 0.382 g (0.002 mol) of 3,5-dichlorobenzoic acid in 5 ml of anhydrous dimethoxyethane. After 15 min was added 0.45 ml (0.003 mol) of phenyldichlorophosphate dropwise with stirring. After 30 min the tetrahydrofuran solution prepared in the first step was added. After 15 min at 0° C. the mixture was allowed to warm to room temperature and stir for 12 h. The mixture was then diluted with ethyl acetate and washed once with 10% aqueous sodium hydroxide, once with 10% aqueous hydrochloric acid, once with water, brine, and dried over anhydrous magnesium sulfate. Filtration and removal of solvents gave a crude solid which was purified by flash- column chromatography (Merck 60 ® silica gel, ethyl acetate/hexane eluant) to give 0.34 g (44% yield) of N-octyl-cis-3-[(3,5- dichlorobenzoyl)thio]acrylamide as a pale yellow solid, mp. 99°–102° C., as reported in Table 1.

The above procedure was repeated with one of the following carboxylic acids replacing 3,5-dichlorobenzoic acid: nicotinic acid; fumaric acid, monoethyl ester; 11-cyanoundecanoic acid, 2,4-hexadienoic acid, ethoxyacetic acid, and 1-methyl-2-pyrrolecarboxylic acid to give the compounds of examples 55 and 57–61, respectively.

EXAMPLE 63

To a cooled (0° C.), stirred solution of 2.13 g (0.010 mol) of 2-octyl-4-isothiazolin-3-one in 20 ml of anhydrous tetrahydrofuran under nitrogen was added 2.05 ml (0.002 mol) of a 1.0M solution of lithium aluminum hydride in tetrahydrofuran. The mixture was stirred at 0° C. for 20 min and then used in the next step as described below.

To a stirred, cooled (0° C.) slurry of 0.26 g (0.011 mol) of hexane-washed sodium hydride in 5 ml of anhydrous tetrahydrofuran under nitrogen was added dropwise a solution of 0.86 ml (0.010 mol) of vinylacetic acid in 5 ml of anhydrous tetrahydrofuran. After 15 min was added 1.59 ml (0.011 mol) of diethyl chlorophosphate dropwise with stirring. After 30 min the tetrahydrofuran solution prepared in the first step was added. After 15 min at 0° C. the mixture was allowed to warm to room temperature and stir for 12 h. The mixture was then diluted with ethyl acetate and washed once with 10% aqueous sodium hydroxide, once with 10% aqueous hydrochloric acid, once with saturated aqueous sodium bicarbonate, brine, and dried over anhydrous magnesium sulfate. Filtration and removal of solvents gave a crude mixture which was purified by chromatography (Merck 60 silica gel, 25% ethyl acetate/hexane eluant) to give 0.61 g (22% yield) of N-octyl-cis-3-[(3-butenoyl)thio]acrylamide as a white solid, m.p. 60°–62° C., as reported in Table 1.

The above procedure was repeated, with the substitution of one of the following acids for the vinylacetic acid: 3-furoic acid, 4-vinylbenzoic acid, 3-thiophenecarboxylic acid, 3-(2-thienyl)acrylic acid, 3-carboxyphenylisothiocyanate, pinonic acid, quinaldic acid, indole-3-carboxylic acid, 3-phenylbutyric acid, 3-phenoxypropionic acid, 4-phenylbutyric acid, ferrocenecarboxylic acid, 2-phenylcinnamic acid, 4-pentenoic acid, trans-2-pentenoic acid, and 2-octynoic acid to give the compounds of examples 62,64–67, 75–84, and 86, respectively.

EXAMPLE 68

To a cooled (0° C.), stirred solution of 2.0 g (0.0094 mol) of 2-octyl-4-isothiazolin-3-one in 25 ml of anhydrous tetrahydrofuran under nitrogen was added 2.6 ml (0.0026 mol) of a 1.0M solution of lithium aluminum hydride in tetrahydrofuran. The mixture was stirred at 0° C. for 20 min and then used in the next step as described below.

To 0.226 g (0.0094 mol) of hexane-washed sodium hydride in 15 ml of anhydrous tetrahydrofuran under nitrogen was added dropwise a solution of 1.3 g (0.0094 mol) of furylacrylic acid in 35 ml of anhydrous tetrahydrofuran. After hydrogen evolution had ceased the mixture was heated to reflux for 1.5 hr and then cooled to 0° C. To this cooled solution was added 1.79 ml (0.0094 mol) of diphenylphosphinic chloride dropwise with stirring. After 5 min the mixture was warmed to room temperature and stirred for 30 min. The mixture was then cooled once again to 0° C. and the tetrahydrofuran solution prepared in the first step was added. After 15 min at 0° C. the mixture was allowed to warm to room temperature and stir for 12 hr. The mixture was then diluted with ethyl acetate and washed once with 10% aqueous sodium hydroxide, once with 10% aqueous hydrochloric acid, once with water, brine, and dried over anhydrous magnesium sulfate. Filtration and removal of solvents gave yellow crystals which were triturated with 5% ethyl acetate/hexane to afford 1.74 g (55% yield) of N-octyl-cis-3-[(trans-3-(2-furan)-propenoyl)thio]acrylamide as a powder, m.p. 86°–92° C., and is reported in Table 1.

The above procedure was employed to make other compounds by using one of the following carboxylic acids instead of furylacetic acid: trans-4-(trifluoromethyl)cinnamic acid, quinoline-3-carboxylic acid, isoquinoline-1-carboxylic acid, 1,2,3,4-tetrahydro-2-naphthanoic acid, and methoxyacetic acid to give the compounds of examples 70, 72–74, and 87, respectively.

EXAMPLE 90

To a stirred, cooled (0° C.) solution of 1.0 ml (0.01625 mol) of propiolic acid in 12 ml of absolute ethanol under nitrogen was added 0.22 ml (0.0016 mol) of triethylamine. After 5 min, 1.45 ml (0.0203 mol) of thioacetic acid was added. After 20 h at 0° C. the reaction mixture was stripped of solvents to give 2.8 g of cis-3-(acetylthio)-propenoic acid as a waxy solid. This product was used in the next step without further purification.

To a mixture of 2.8 g (0.0162 mol) of cis-3-(acetylthio)propenoic acid and 0.1 ml of N,N-dimethylformamide in 50 ml of toluene under nitrogen was added 2.84 ml (0.0325 mol) of oxalyl chloride. After 3 h the solvents were removed to give cis-3-(acetylthio)propenoyl chloride. This crude product was used in the next step without any further purification.

To a stirred, cooled (0° C.) solution of 3.0 g (0.0162 mol) of cis-3-(acetylthio)propenoyl chloride in 30 ml of dichloromethane under nitrogen was added dropwise 2.98 g (0.0163 mol) of cyclododecylamine as a solution in 30 ml of dichloromethane. After 15 min, 2.27 ml (0.0163 mol) of triethylamine was added dropwise. After 12 h the reaction mixture was poured into water and extracted three times with dichloromethane. The combined organic layers were washed with water, brine, and dried over magnesium sulfate. Filtration and removal of solvents gave 4.5 g of a 2:1 mixture of cis and trans isomers as a tan solid. Purification by flash column chromatography (Merck 60® silica gel, ethyl acetate/hexane eluant) gave 0.5 g (10% yield) of N-cyclododecyl-cis-3-(acetylthio)acrylamide as a white powder where NMR is reported in Table 2.

EXAMPLE 113

To a stirred, cooled (0° C.) solution of 15.4 ml (0.25 mol) of propiolic acid in 200 ml of absolute ethanol under nitrogen was added 3.48 ml (0.025 mol) of triethylamine. After 5 min, 33 ml (0.28 mol) of thiobenzoic acid was added very cautiously and dropwise. The exothermic reaction led to the ethanol reaching reflux despite the ice-water bath. After 15 min a solid precipitated from the orange solution. After 2 h at 0° C. the reaction mixture was filtered and the solid was washed twice with absolute ethanol and twice with chloroform to afford 18.3 g (35% yield of cis-3-(benzoylthio)-propenoic acid as a white powder.

To a mixture of 7.0 g (0.0336 mol) of cis-3-(benzoylthio)propenoic acid and 0.5 ml of N,N-dimethylformamide in 100 ml of dichloromethane under nitrogen was added 2.93 ml (0.0336 mol) of oxalyl chloride. After 12 h the solvents were removed to give 7.5 g (99% yield) of cis-3-(benzoylthio)propenoyl chloride as a pale yellow solid.

To a stirred, cooled (0° C.) solution of 0.70 g (0.0039 mol) of cis-3-(benzoylthio)propenoyl chloride in 40 ml of dichloromethane under nitrogen was added dropwise 0.21 ml (0.0039 mol) of propargylamine as a solution in 10 ml of dichloromethane. After 15 min, 0.43 ml (0.0039 mol) of triethylamine was added dropwise. The reaction was allowed to stir at 0° C. for 2 h, poured into 10% aqueous hydrochloric acid, and extracted three times with ethyl acetate. The combined organic layers were washed with water, brine, and dried over magnesium sulfate. Filtration and removal of solvents gave 0.49 g (65% yield) of N-(2-propynyl)-cis-3-(benzoylthio)acrylamide as a white powder, m.p. 131°–134° C., as described in Table 1.

The above procedure was used for other analogs by replacing the propargylamine with one of the following amines: 1,1,3,3-tetramethylbutylamine, and 4-(aminoethyl)morpholine to give compounds of examples 114 and 116, respectively.

TABLE 2

| | PROTON NMR DATA FOR CERTAIN EXAMPLES | |
|---|---|---|
| Compound No. | {200 MHz, delta scale in ppm, tetramethylsilane (TMS) standard, Chloroform-d (CDCL$_3$) solvent unless otherwise noted} | Method of Preparation Example No. |
| 1 | 0.9 (t, 3H), 1.1–1.4 (m), 1.57 (m), 3.35 (q, 2H), 6.1 (br t, 1H), 6.1 (d, 1H), 7.43–7.7 (m, aromatic H), 7.9 (d, 1H), 8.1 (m, aromatic H). | 3 |
| 2 | 0.9 (t, 3H), 1.1–1.4 (m), 1.6 (m), 3.3 (br q, 2H), 3.7 (s, 2H), 4.2 (q, 2H), 6.35 (d, 1H), 7.45 (br t, 1H), 7.55 (d, 1H). | 9 |
| 5 | 0.9 (t, 3H), 1.1–1.4 (m), 1.6 (m), 3.3 (m, 2H), 6.2 (d, 1H), 6.4 (br t, 1H), 7.3–8.0 (m, aromatic H), 7.75 (d, 1H). | 3 |
| 6 | 0.9 (t, 3H), 1.1–1.4 (m), 1.5–1.6 (m), 3.3 (br q, 2H), 6.4 (d, 1H), 7.25 (br t, 1H), 7.45 (m, aromatic H), 7.75 (d, 1H), 8.1 (d, aromatic H), 8.57 (d, aromatic H). | 9 |
| 8 | 0.9 (t, 3H), 1.1–1.4 (m), 1.5–1.6 (m), 3.35 (br q, 2H), 3.85 (s, 3H), 6.2 (d, 1H), 6.35 (br t, 1H), 7.15 (d, aromatic H), 7.4 (t, aromatic H), 7.55 (d, aromatic H), 7.7 (d, aromatic H), 7.9 (d, 1H). | 9 |
| 11 | 0.9 (t, 3H), 1.0 (m), 1.1–1.4 (m), 1.5–1.8 (m), 2.6 (m, 2H), 3.25 (q, 2H), 6.05 (d, 1H), 6.5 (br t, 1H), 7.55 (d, 1H). | 9 |
| 12 | 0.8 (t, 3H), 1.1–1.6 (m, 12H), 3.2 (q, 2H), 3.92 (s, 2H), 6.0 (br s, 1H), 6.02 (d, 1H), 7.3 (s, 5H), 7.6 (d, 1H). | 12 |
| 15 | 0.9 (t, 3H), 1.1–1.6 (m), 3.3 (q, 2H), 6.3 (d, 1H), 6.6 (m, aromatic H), 6.65 (br m, 1H), 7.38 (d, aromatic H), 7.7 (d, aromatic H), 7.83 (d, 1H). | 9 |
| 20 | 0.9 (t, 3H), 1.1–1.6 (m), 2.0 (d, 3H), 3.3 (q, 2H), 5.75 (m, 1H), 6.1 (d, 1H), 6.15 (br t, 1H), 6.25 (d, 1H), 7.73 (d, 1H). | 10 |
| 24 | 0.9 (t, 3H), 1.1–1.6 (m), 3.0–3.3 (m, 2H), 3.35 (q, 2H), 3.7–3.9 (m, 2H), 6.1 (d, 1H), 7.65 (d, 1H). | 10 |
| 27 | 0.9 (m, 9H), 1.1–1.4 (m), 1.4–1.9 (m), 2.6 (m, 1H), 3.35 (q, 2H), 6.0 (br t, 1H), 6.05 (d, 1H), 7.7 (d, 1H). | 10 |
| 30 | 0.9 (t, 3H), 1.1–1.6 (m), 3.35 (q, 2H), 3.95 (s, 3H), 6.1 (br t, 1H), 6.2 (d, 1H), 7.6 (d, 1H). | 10 |
| 31 | 0.9 (t, 3H), 1.1–1.6 (m), 3.35 (q, 2H), 4.3 (s, 2H), 6.05 (d, 1H), 6.15 (br t, 1H), 7.6 (d, 1H). | 10 |
| 34 | 0.9 (t, 3H), 1.1–1.6 (m), 3.3 (q, 2H), 3.35 (s, 2H), 3.75 (s, 3H), 5.95 (d, 1H), 6.3 (br t, 1H), 6.95 (d, 1H). | 10 |
| 35 | 0.9 (t, 3H), 1.1–1.6 (m), 3.3 (q, 2H), 4.9 (s, 2H), 6.25 (d, 1H), 6.55 (br t, 1H), 7.4–7.6 (m), 7.8 d (1H), 8.0 (d, aromatic H). | 10 |
| 37 | 0.9 (t, 3H), 1.1–1.6 (m), 3.35 (2H), 6.1 (s, 1H), 6.3 (d, 1H), 6.45 (br t, 1H), 7.55 (d, 1H). | 10 |
| 38 | 0.9 (t, 3H), 1.1–1.4 (m), 1.5 (m), 1.5 (d, 3H), 3.3 (q, 2H), 3.55 (q, 1H), 3.75 s, 3H), 5.9 (d, 1H), 6.05 (br t, 1H), 7.1 (d, 1H). | 10 |
| 39 | 0.9 (t, 3H), 1.1–1.6 (m), 2.85–3.1 (m, 2H), 3.25 (q, 2H), 3.75 (s, 3H), 4.0 (d, 2H), 4.15 (m, 1H), 5.8 (d, 1H), 5.8 (br t, 1H), 6.35 (s, aromatic H), 6.9 (d, 1H), 7.4 (s, aromatic H) | 40 |
| 42 | 0.9 (t, 3H), 1.1–1.6 (m), 3.25 (q, 2H), 3.9–4.3 (m, 3H), 5.85 (d, 1H), 5.95 (br t, 1H), 6.35 (s, aromatic H), 6.9 (d, 1H), 7.4 (s, aromatic H). | 40 |
| 47* | 0.6 (t, 3H), 0.8–1.4 (m), 2.6 (m, 1H), 2.9 (m, 1H), 3.0 (m, 2H), 3.2 (m, 1H), 5.9 (d, 1H), 6.8 (d, 1H). | 47 |
| 48 | 0.9 (t, 3H), 1.1–1.6 (m), 3.35 (q, 2H), 5.85 (br t, 1H), 6.15 (d, 1H), 7.3 (d, aromatic H), 7.85 (d, 1H), 8.1 (d, aromatic H). | 10 |
| 50 | 0.9 (t, 3H), 1.1–1.6 (m), 2.6 (s, 3H), 3.45 (br q, 2H), 6.3 (d, 1H), 6.8 (br m, 1H), 7.0 (d, aromatic H), 7.5 (d, aromatic H), 7.85 (1H). | 10 |
| 53 | 0.9 (t, 3H), 1.1–1.6 (m), 3.35 (q, 2H), 6.0 (br t, 1H), 6.25 (d, 1H), 7.85 (d, 1H), 8.5 (s, 1H), 8.9 (s, 1H), 9.2 (s, 1H). | 54 |
| 61 | 0.9 (t, 3H), 1.1–1.6 (m), 3.35 (q, 2H), 3.95 (s, 3H), 6.0 (br t, 1H), 6.1 (d, 1H), 6.15 (m, aromatic H), | 54 |

TABLE 2-continued
PROTON NMR DATA FOR CERTAIN EXAMPLES

| Compound No. | {200 MHz, delta scale in ppm, tetramethylsilane (TMS) standard, Chloroform-d (CDCL$_3$) solvent unless otherwise noted} | Method of Preparation Example No. |
|---|---|---|
|  | 6.9 (m, aromatic H), 7.3 (m, aromatic H), 7.85 (d, 1H). |  |
| 62 | 0.9 (t, 3H), 1.1–1.6 (m), 3.35 (q, 2H), 6.1 (m, 1H), 6.15 (d, 1H), 6.9 (s, aromatic H), 7.55 (m, aromatic H), 7.85 (d, 1H), 8.25 (m, aromatic H). | 63 |
| 64 | 0.9 (t, 3H), 1.1–1.6 (m), 3.35 (q, 2H), 5.5 (m, 1H), 5.8–6.0 (m, 1H), 6.0 (br t, 1H), 6.2 (d, 1H), 6.7–6.9 (m, 1H), 7.5 (m, aromatic H), 7.9 (d, 1H), 8.0–8.2 (m, aromatic H). | 63 |
| 66 | 0.9 (t, 3H), 1.1–1.6 (m), 3.35 (q, 2H), 5.8 (br t, 1H), 6.1 (d, 1H), 6.6 (d, 1H), 7.1 (m, aromatic H), 7.35 (d, aromatic H), 7.5 (d, aromatic H), 7.35 (d, aromatic H), 7.5 (d, aromatic H), 7.85 (d, 1H), 7.95 (d, 1H). | 63 |
| 71 | 0.9 (t, 3H), 1.1–1.6 (m), 3.3 (q, 2H), 5.8 (m, 1H), 5.85 (m, 1H), 6.08 (d, 1H), 6.5 (m, 2H), 7.75 (d, 1H). | 10 |
| 73 | 0.9 (t, 3H), 1.1–1.6 (m), 3.35 (q, sH), 5.8 (br t, 1H), 6.15 (d, 1H), 7.8 (m, aromatic H), 7.9 (m, aromatic H), 7.95 (d, 1H), 8.65 (m, aromatic H), 9.2 (m, aromatic H). | 68 |
| 78 | 0.9 (t, 3H), 1.1–1.6 (m), 2.45 (m, 2H), 2.8 (m, 2H), 3.35 (q, 2H), 5.1 (m, 2H), 5.8 (m, 1H), 5.9 (m, 1H), 6.05 (d, 1H), 7.65 (d, 1H). | 63 |
| 79 | 0.9 (t, 3H), 1.1–1.6 (m), 3.1 (t, 2H), 3.3 (q, 2H), 4.3 (t, 2H), 5.95 (br t, 1H), 6.05 (d, 1H), 6.95 (m), 7.3 (m), 7.65 (d, 1H). | 63 |
| 85 | 0.9 (t, 3H), 1.1–1.6 (m), 2.05 (m, 2H), 2.4 (t, 2H), 2.75 (t, 2H), 3.3 (q, 2H), 3.7 (s, 3H), 6.0 (br t, 1H), 6.05 (d, 1H), 7.65 (d, 1H). | 10 |
| 86 | 0.9 (t, 3H), 1.1–1.6 (m), 2.45 (m, 2H), 3.35 (q, 2H), 5.95 (br s, 1H), 6.05 (d, 1H), 7.75 (d, 1H). | 63 |
| 87 | 0.9 (t, 3H), 1.1–1.6 (m), 3.4 (q, 2H), 3.5 (s, 3H), 4.2 (s, 2H), 5.95 (m, 1H), 6.1 (d, 1H), 7.65 (d, 1H). | 68 |
| 89 | 0.9 (t, 3H), 1.1–1.4 (m), 1.5 (s, 6H), 2.6 (s, 2H), 3.35 (q, 2H), 5.9 (br m, 1H), 6.15 (m, 1H), 6.15 (d, 1H), 7.75 (d, 1H). | 10 |
| 90 | 1.0–1.8 (m, 22H), 2.42 (s, 3H), 4.12 (m, 1H), 5.5 (br d, 1H), 5.95 (d, 1H), 7.6 (d, 1H). | 90 |
| 91 | 0.9 (t, 3H), 1.1–1.6 (m), 3.4 (q, 2H), 5.75 (br t, 1H), 6.05 (d, 1H), 7.3–7.7 (m, aromatic H), 7.8 (d, 1H). | 10 |
| 96 | 0.9 (t, 3H), 1.1–1.6 (m), 3.35 (q, 2H), 5.9 (br t, 1H), 6.1 (d, 1H), 6.9 (d, 1H), 7.8 (d, 1H), 7.8 (d, 1H), 7.8 (m, aromatic H), 8.3 (m, aromatic H). | 10 |
| 101 | 0.9 (t, 3H), 1.1–1.6 (m) 2.7 (s, 3H), 2.9 (m), 3.3 (q, 2H), 3.9 (m, 1H), 5.4–6.0 (m, 1H), 5.9 (br s, 1H), 6.0 (d, 1H), 7.6 (d, 1H). | 10 |
| 103 | 0.9 (t, 3H), 1.1–1.6 (m), 3.4 (q, 2H), 6.0 (br s, 1H), 6.2 (d, 1H), 7.6 (d, aromatic H), 7.85 (d, 1H), 7.9 (m, aromatic H), 8.2 (m, aromatic H). | 10 |
| 105 | 0.9 (t, 3H), 1.1–1.6 (m), 3.35 (q, 2H), 4.0 (s, 3H), 5.9 (br t, 1H), 6.2 (d, 1H), 7.6–7.9 (m, aromatic H), 7.85 (d, 1H). | 10 |
| 110 | 0.9 (t, 3H), 1.1–1.7 (m), 2.3 (t, 2H), 2.7 (t, 2H), 3.3 (q, 2H), 3.7 (s, 3H), 6.1 (d, 1H), 6.1 (br s, 1H), 7.6 (d, 1H). | 10 |
| 114 | 1.0 (s, 9H), 1.5 (s, 6H), 1.8 (s, 2H), 5.5 (br s, 1H), 6.05 (d, 1H), 7.4–7.6 (m, aromatic H), 7.85 (d, 1H), 8.1 (m, aromatic H). | 113 |
| 115 | 0.85 (dt, 3H), 1.1–1.7 (m), 2.68 (t, 2H), 3.35 (q, 2H), 6.05 (br t, 1H), 6.18 (d, 1H), 7.3 (d, aromatic H), 7.9 (d, 1H), 8.02 (d, aromatic H). | 10 |
| 116 | 2.5 (m), 3.5 (q, 2H), 3.8 (m), 6.2 (d, 1H), 6.4 (br s, 1H), 7.5–7.7 (m, aromatic H), 7.95 (d, 1H), 8.1 (m, aromatic H). | 113 |
| 119 | 0.9 (t, 3H), 1.1–1.8 (m), 2.3 (t), 2.7 (t), 3.35 (q, 2H), 3.7 (s, 3H), 5.7 (br t, 1H), 6.0 (d, 1H), 7.65 (d, 1H). | 10 |

*D$_2$O and NaOD used as solvent and internal standard.

EXAMPLE A: BIOCIDE TEST PROCEDURES

A minimum inhibitory concentration (MIC) value is obtained using a broth, two-fold serial dilution test performed as follows: A stock solution or dispersion of the test compound, typically at a concentration of 1%, is made in a 5:3:2 solvent solution of acetone, methanol, and water. A volume of the stock solution is dispensed into culture media to give an initial starting test concentration of 500 ppm compound.

When the test is ready to be done, each vessel in the dilution series, except the first vessel, contains an equal volume of compound free broth. The first vessel contains twice the volume of broth with the starting concentration of test compound. One half of the broth from the first vessel is transferred to the second vessel. After being mixed, one half the resulting volume is removed from the second vessel and transferred to the third vessel. The entire cycle is repeated sufficiently to give a series of concentrations amounting to 500, 250, 125, 63, 31, 16, 8, and 4 ppm, respectively.

Each vessel is then inoculated with a cell suspension of the appropriate test organism. Bacteria are grown in broth and fungi on agar slants for a time and at a temperature appropriate to the species being tested. At the end of the growth period, the broth is vortexed to disperse the cells. In the case of fungi, the spores are harvested by pipetting water onto the slant and dislodging the spores with a sterile loop. The cell/spore suspension is standardized by controlling incubation time, temperature, and the volume of the diluent. The suspension is then used to inoculate the vessels containing the broth compound. The vessels are then incubated at the appropriate temperature. After the incubation, the vessels are examined for growth/no growth. The minimum inhibitory concentration (MIC) is defined as the lowest concentration of compound that results in complete inhibition of growth of the test organism.

The organisms tested to demonstrate biocidal activity include:
BACTERIA:
*Pseudomonas fluorescens* (Ps.fl), gram negative
*Pseudomonas aerugenosa* (Ps.ae), gram negative
*Escherichia coli* (E.c), gram negative
*Staphylococcus aureus* (S.a), gram positive
FUNGI:
*Aspergillus niger* (A.n)
*Aureobasidium pullulans* (A.p)

The results of the test are shown below in Table 3.

TABLE 3

| Compound | A.n | A.p | E.c | Ps.ae | Ps.fl | S.a |
|---|---|---|---|---|---|---|
| 9 | >500 | <4 | >500 | >500 | >500 | >500 |
| 10 | 125 | <4 | >500 | >500 | 16 | <4 |
| 11 | 250 | <4 | >500 | >500 | >500 | >500 |
| 41 | >500 | >500 | >500 | >500 | >500 | ≧500 |
| 43 | >500 | 16 | >500 | >500 | >500 | >500 |
| 47 | >500 | >500 | >500 | >500 | >500 | >500 |
| 115 | >500 | ≧250 | >500 | >500 | >500 | >500 |

The compounds of Examples 1-8, 12-26, 28-33, 36-37, 39-42, 44-109, 111-114, and 116-120 were subjected also to the following alternate biocidal activity test procedures with the results as indicated in Table 4.

Speed of Kill Test

An acetone solution of the compound was prepared at 10,000 ppm and 0.1 ml was added to 9.8 ml of SHW. 0.1 ml of Ps fl inoculum at 10,000,000 cells per ml was added to the SHW, providing 10 ml of solution which was incubated for 24 hours prior to recovery into Tryptic Soy Broth (TSB).

To recover and measure the living cells, 2.5 ml of the SHW mix was transferred to a reservoir from which 2.5 µl was then transferred 8 times to microtiter wells containing 225 µl of TSB. Each of the 8 transfers was then serially diluted seven times, providing eight replicates of eight dilutions. The concentration at which no living cells were recovered was used to back calculate the log reduction. The data was entered into the database, and the log reductions calculated automatically.

Minimum Inhibitory Concentration Test

The MIC test measures the viability of Pseudomonas fluorescens inoculum in TSB when exposed for 72 hours to varying concentrations of test compound.

A 125 µl aliquot of 10,000 ppm test compound in acetone was added to 4.88 ml of TSB to provide a 250 ppm solution. From this solution, 100 µL was transferred to the first row of two microtiter plate columns. Both replicates and five additional compounds were all serially diluted 1:1 to a final concentration of 0.8 ppm in TSB.

Inoculation was accomplished by diluting a 24 hr Ps fl culture, four mls per 36 mls of phosphate buffer solution. A Dynatech autoinoculator was used to transfer 1.5 µl of this cell suspension to the microtiter plates. The plates were incubated at 30° C. for 3 days before the lowest concentration at which no growth occurs was recorded in the database. The MIC test data on Ps.fl, Ps.ae, E.c, and S.a. bacteria and Candida albicans (C.alb), A.n and A.p fungi are listed in Table 4.

TABLE 4

MIC Test Results in Ppm*

| Compound | A.n | A.p | C.alb | E.c | Ps.ae | Ps.fl | S.a |
|---|---|---|---|---|---|---|---|
| 1 | | | | | | >250 | |
| 2 | | | | | | >250 | |
| 3 | | | | | | >250 | |
| 4 | | | | | | >250 | |
| 5 | | | | | | >250 | |
| 6 | | | | | | >250 | |
| 7 | | | | | | >250 | |
| 8 | | | | | | >250 | |
| 12 | | | | | | >250 | |
| 13 | | | | | | >250 | |
| 14 | | | | | | >250 | |
| 15 | | | | | | >250 | |
| 16 | | | | | | >250 | |
| 17 | | | | | | >250 | |
| 18 | | | | | | >250 | |
| 19 | | | | | | >250 | |
| 20 | | | | | | >250 | |
| 21 | | | | | | >250 | |
| 22 | | | | | | >250 | |
| 23 | | | | | | >250 | |
| 24 | 63 | <2 | 12 | >250 | >250 | >250 | >250 |
| 25 | | | | | | >250 | |
| 26 | | | | | | >250 | |
| 28 | | | | | | >250 | |
| 29 | | | | | | >250 | |
| 30 | | | | | | >250 | |
| 31 | | | | | | >250 | |
| 32 | | | | | | >250 | |
| 33 | | | | | | >250 | |
| 36 | | | | | | >250 | |
| 37 | | | | | | >250 | |
| 39 | | | | | | >250 | |
| 40 | | | | | | >250 | |
| 41 | | | | | | >250 | |
| 42 | | | | | | >250 | |
| 44 | | | | | | >250 | |
| 45 | | | | | | >250 | |
| 46 | | | | | | >250 | |
| 47 | | | | | | >250 | |
| 48 | | | | | | >250 | |
| 49 | | | | | | >250 | |
| 50 | | | | | | >250 | |
| 51 | | | | | | >250 | |
| 52 | | | | | | >250 | |
| 53 | | | | | | >250 | |
| 54 | | | | | | >250 | |
| 55 | | | | | | >250 | |
| 56 | | | | | | >250 | |
| 57 | | | | | | >250 | |
| 58 | | | | | | >250 | |
| 59 | | | | | | >250 | |
| 60 | | | | | | >250 | |
| 61 | | | | | | >250 | |
| 62 | | | | | | >250 | |
| 63 | | | | | | >250 | |
| 64 | | | | | | >250 | |
| 65 | | | | | | >250 | |
| 66 | | | | | | >250 | |

TABLE 4-continued

MIC Test Results in Ppm*

| Compound | A.n | A.p | C.alb | E.c | Ps.ae | Ps.fl | S.a |
|---|---|---|---|---|---|---|---|
| 67 | | | | | | >250 | |
| 68 | | | | | | >250 | |
| 69 | | | | | | >250 | |
| 70 | | | | | | >250 | |
| 71 | | | | | | >250 | |
| 72 | | | | | | >250 | |
| 73 | | | | | | >250 | |
| 74 | | | | | | >250 | |
| 75 | | | | | | >250 | |
| 76 | | | | | | >250 | |
| 77 | | | | | | >250 | |
| 78 | | | | | | >250 | |
| 79 | | | | | | >250 | |
| 80 | | | | | | >250 | |
| 81 | | | | | | >250 | |
| 82 | | | | | | >250 | |
| 83 | | | | | | >250 | |
| 84 | | | | | | >250 | |
| 85 | | | | | | >250 | |
| 86 | | | | | | >250 | |
| 87 | | | | | | >250 | |
| 88 | | | | | | >250 | |
| 89 | | | | | | >250 | |
| 90 | | | | | | >250 | |
| 91 | | | | | | >250 | |
| 92 | | | | | | >250 | |
| 93 | | | | | | >250 | |
| 94 | | | | | | >250 | |
| 95 | | | | | | >250 | |
| 96 | | | | | | >250 | |
| 97 | | | | | | >250 | |
| 98 | | | | | | >250 | |
| 99 | | | | | | >250 | |
| 100 | | | | | | >250 | |
| 101 | | | | | | >250 | |
| 102 | | | | | | >250 | |
| 103 | | | | | | >250 | |
| 104 | | | | | | ≧250 | |
| 105 | 24 | <2 | <2 | >250 | >250 | ≧125 | >250 |
| 106 | | | | | | >250 | |
| 107 | | | | | | >250 | |
| 108 | | | | | | >250 | |
| 109 | | | | | | >250 | |
| 111 | | | | | | >250 | |
| 112 | | | | | | >250 | |
| 113 | ≧250 | 31 | ≧125 | 31 | 125 | 63 | 63 |
| 114 | | | | | | >250 | |
| 115 | | | | | | >250 | |
| 116 | | | | | | >250 | |
| 117 | | | | | | I** | |
| 118 | | | | | | I** | |
| 119 | | | | | | I** | |
| 120 | | | | | | I** | |

*Blank space = not tested
**I = inactive

EXAMPLE B: FUNGICIDE TEST METHODS

The compounds of this invention were tested for fungicidal activity in vivo against cucumber downy mildew (CDM), rice blast (RB), rice sheath blight (RSB), tomato late blight (TLB), wheat powdery mildew (WPM), wheat stem rust (WSR) and wheat leaf rust (WLR). In test on cereals (except for rice plants used for testing rice blast), the plants were trimmed about 24 hours prior to the application of the fungicide compound to provide a uniform plant height and to facilitate uniform application of the compound and inoculation with the fungus. The compounds were dissolved in a 2:1:1 mixture of water acetone, and methanol, sprayed onto the plants, allowed to dry (four to six hours), and then the plants were inoculated with the fungus. Each test utilized control plants which were sprayed with the water, acetone, and methanol mixture and inoculated with the fungus. The remainder of the technique of each of the tests is given below and the results are reported as percent disease control (percentages of plants treated with the compounds of the present invention lacking disease signs or symptoms compared to the untreated control plants).

Cucumber Downy Mildew (CDM):

Pseudoperonospora cubensis was maintained on leaves of live Marketer cucumber plants in a constant temperature room at 65° F. to 75° F. in humid air with moderate light intensity for 7 to 8 days. A water suspension of the spores from infested leaves was obtained and the spore concentration was adjusted to about 100,000 per ml of water.

Marketer cucumber seedlings were inoculated by spraying the underside of the leaves with a DeVilbiss atomizer until small droplets were observed on the leaves. The inoculated plants were incubated in a mist chamber for 24 hours at about 70° F. and then subsequently incubated for 6 to 7 days in a controlled temperature room under mist at 65° F. to 75° F. Seven days after inoculation, the percent disease control was determined.

Rice Blast (RB):

Nato rice plants were inoculated with Piricularia oryzae (about 20,000 conidia per ml) by spraying the leaves and stems with an airbrush until a uniform film of inoculum was observed on the leaves. The inoculated plants were incubated in a humid environment (75° F. to 85° F.) for about 24 hours, then placed in a greenhouse environment (70° F. to 75° F.). Seven to eight days after inoculation, the percent disease control was determined.

Rice Sheath Blight (RSB):

Pellicularia filamentosa (f. sp. sasiki) was cultured on an autoclaved mixture of crushed rice seeds and potato dextrose broth (100 gms of rice seeds per 30 ml of potato dextrose broth) in a 500 ml Erlenmeyer flask. After 10 days, the culture was blended in a blender to produce a uniform inoculum. Approximately one teaspoon of inoculum was spread among Lebonnet rice seedlings on the soil surface of each pot (3 inch diameter). The inoculated seedlings were incubated for 5 days in a humidity cabinet (85° F. to 90° F.). Percent disease controls were determined immediately after removing the seedlings from the cabinet.

Tomato Late Blight (TLB):

Phytophthora infestans was cultured on four week old Pixie tomato plants in a controlled environment room (65° F. to 70° F. and 100% relative humidity). After storage, the spores were washed from the leaves with water and dispersed by DeVilbiss atomizer over three week old Pixie tomato plants which had been sprayed previously with experimental fungicides. The inoculated plants were placed in a humidity cabinet at 70° F. and constant mist for 24 hours for infection. The plants were then moved to the controlled environment room as above and scored after three more days incubation. Disease control levels were recorded as percent control four days after inoculation and five days after spraying the compounds.

Wheat Powdery Mildew (WPM):

Erysiphe graminis (f. sp. tritici) was cultured on Pennol wheat seedlings in a controlled temperature room at 65° F. to 75° F. Mildew spores were shaken from the culture plants onto Pennol wheat seedlings which had been sprayed previously with the fungicide compound. The inoculated seedlings were kept in a controlled temperature room at 65° F. to 75° F. and subirrigated. The percent disease control was rated 8 to 10 days after the inoculation.

Wheat Stem Rust (WSR):

*Puccinia graminis* (f. sp. *tritici* Race 15B-2) was cultured on Wanzer wheat seedlings for a period of 14 days in a greenhouse. A water suspension of the spores from infested plants was obtained and the spore concentration was adjusted to about 200,000 spores per ml of deionized water. Wanzer wheat plants which had been previously treated with the fungicide compounds were inoculated by applying the stem rust spore suspension, until runoff, with a DeVilbiss atomizer at 5 lbs. per square inch air pressure. After inoculation, the plants were placed in a humid environment at approximately 75° F. where they were exposed to 12 hours of continuous darkness followed by a minimum of 3 to 4 hours of light having an intensity of about 500 footcandles. The temperature in the chamber did not exceed 85° F. At the end of the light period, the plants were placed in a greenhouse where they were permitted to grow for a period of two weeks at which time the percent disease control was determined.

Wheat Leaf Rust (WLR):

*Puccinia recondita* (f. sp. *tritici* Races PKB and PLD) was increased on seven day old wheat (cultivar Fielder) over a 14 day period in the greenhouse. Spores were collected from the leaves with a cyclone vacuum or by setting on aluminum foil. The spores were cleaned by sieving through a 250 micron opening screen and stored or used fresh. Storage employed sealed bags in an Ultra-low freezer. When stored, spores must be heat shocked for two minutes at 40° F. before use. A spore suspension is prepared from dry uredia by adding 20 mg (9.5 million) per ml of Soltrol oil. The suspension is dispensed into gelatin capsules (0.7 ml capacity) which attach to the oil atomizers. One capsule is used per flat of twenty of the two inch square pots of seven day old Fielder wheat. After waiting for at least 15 minutes for the oil to evaporate from the wheat leaves, the plants are placed in a dark mist chamber (18°-20° C. and 100% relative humidity) for 24 hours. The plants are then put in the greenhouse for the latent period and scored after 10 days for disease levels. Protective and curative tests were inoculated one day after and two days, respectively, before spraying the plants with the test chemicals.

Selected compounds of Examples 1–120 were subjected also to the following in vitro fungitoxicity assay against *Pythium ultimum* in a liquid culture, with the results as indicated in Table 6.

*Pythium ultimum* Fungitoxicity Assay

A dilution series of the test compound was prepared in dimethylsulfoxide, and 0.1 ml of each dilution was added to 19.9 ml of a liquid asparagine-sucrose medium (D. C. Erwin and K. Katznelson (1971), Can. J. Microbiol. 7, 15) in 9 cm diameter petri dishes to give the desired final concentrations of test compound. Plates were inoculated with mycelial plugs, 7 mm diameter, taken from the growing edge of 48 h old cultures of *Pythium ultimum*, (ATCC 26083), grown on potato dextrose agar. Two replicate plates were used for each treatment. The increase in mycelial dry weight was determined after growth for 48 h at 25° C. with shaking at 60 rpm. EC50 values were calculated from dose response curves.

TABLE 5

| | | % Control* versus Assorted Fungi | | | | | |
|---|---|---|---|---|---|---|---|
| Compound | CDM | RB | RSB | TLB | WLR | WPM | WSR |
| 1 | — | 0/100 | 0/100 | 100/100 | 0/100 | 0/100 | — |
| 2 | — | 50/6 | 0/100 | 90/100 | 0/100 | 0/100 | — |
| 3 | 85/50 | 80/100 | 0/100 | 90/100 | 0/100 | 0/100 | 75/200 |
| 4 | 99/50 | 80/100 | 0/100 | 90/100 | 0/100 | 0/100 | 50/200 |
| 5 | 50/50 | 80/25 | 0/100 | 90/100 | 0/100 | 0/100 | 75/200 |
| 6 | 85/50 | 50/100 | 0/100 | 90/100 | 0/100 | 0/100 | 90/200 |
| 7 | — | — | 50/6 | 0/100 | 0/100 | 0/100 | — |
| 8 | — | 80/100 | 0/100 | 80/100 | 0/100 | 0/100 | — |
| 9 | — | 90/100 | 0/100 | 90/100 | 0/100 | 0/100 | — |
| 10 | 85/50 | 80/100 | 0/100 | 90/100 | 50/100 | 0/100 | 90/200 |
| 11 | 85/50 | 75/50 | 0/100 | 90/100 | 50/100 | 0/100 | 90/200 |
| 12 | 85/50 | 90/200 | 0/100 | 90/100 | 0/100 | 0/100 | 90/200 |
| 13 | — | 0/100 | 0/100 | 80/100 | 0/100 | 0/100 | — |
| 14 | 50/50 | 100/100 | 0/100 | 90/100 | 0/100 | 0/100 | 75/200 |
| 15 | 50/50 | 100/100 | 0/100 | 95/100 | 95/100 | 0/100 | 90/200 |
| 16 | 50/12 | 100/25 | 0/100 | 90/100 | 75/100 | 0/100 | 75/100 |
| 17 | 50/50 | 80/100 | 0/100 | 90/100 | 0/100 | 0/100 | 95/200 |
| 18 | 70/50 | 50/100 | 0/100 | 100/25 | 0/100 | 0/100 | 50/200 |
| 19 | — | 0/100 | 0/100 | 90/100 | 0/100 | 0/100 | — |
| 20 | 85/12 | 50/200 | 0/100 | 95/6 | 0/100 | 0/100 | 75/200 |
| 21 | — | 0/100 | 0/100 | 80/100 | 0/100 | 0/100 | — |
| 22 | 99/50 | 0/100 | 0/100 | 95/25 | 0/100 | 0/100 | 75/200 |
| 23 | — | 0/100 | 80/100 | 0/100 | 0/100 | 0/100 | — |
| 24 | — | 0/100 | 0/100 | 95/100 | 0/100 | 0/100 | — |
| 25 | 85/50 | 0/100 | 0/100 | 100/100 | 0/100 | 0/100 | 90/100 |
| 26 | 85/50 | 80/100 | 0/100 | 90/100 | 0/100 | 0/100 | 90/100 |
| 27 | — | 0/100 | 0/100 | 90/100 | 0/100 | 0/100 | — |
| 28 | — | 90/100 | 0/100 | 0/100 | 0/100 | 0/100 | — |
| 29 | 85/50 | 75/200 | 0/100 | 90/100 | 0/100 | 0/100 | 75/200 |
| 30 | 75/50 | 0/100 | 0/100 | 80/100 | 50/25 | 0/100 | 75/200 |
| 31 | — | 0/100 | 0/100 | 80/100 | 0/100 | 0/100 | — |
| 32 | — | 0/100 | 0/100 | 80/100 | 0/100 | 0/100 | — |
| 33 | 50/50 | 80/25 | 0/100 | 80/100 | 0/100 | 85/100 | 75/200 |
| 34 | — | 0/100 | 90/100 | 80/100 | 0/100 | 0/100 | — |
| 35 | — | 80/100 | 0/100 | 0/100 | 0/100 | 85/100 | — |
| 36 | — | 90/25 | 0/100 | 0/100 | 0/100 | 0/100 | — |
| 37 | — | 80/25 | 0/100 | 90/6 | 0/100 | 0/100 | — |
| 38 | — | 80/25 | 0/100 | 80/6 | 0/100 | 0/100 | — |

TABLE 5-continued

| | % Control* versus Assorted Fungi | | | | | | |
|---|---|---|---|---|---|---|---|
| Compound | CDM | RB | RSB | TLB | WLR | WPM | WSR |
| 39 | — | 80/100 | 0/100 | 0/100 | 0/100 | 0/100 | — |
| 40 | 85/50 | 75/200 | 0/100 | 95/100 | 0/100 | 50/100 | 75/200 |
| 41 | 0/200 | 0/200 | 0/200 | 0/200 | 100/25 | 0/200 | — |
| 42 | 50/50 | 90/200 | — | 0/200 | 0/100 | 0/100 | 50/200 |
| 43 | 50/50 | 0/100 | — | 0/100 | 0/100 | 0/100 | 50/200 |
| 44 | 0/200 | 0/200 | 0/200 | 90/200 | 0/200 | 0/200 | 0/100 |
| 45 | 0/200 | 0/200 | 80/200 | 0/200 | 0/200 | 0/200 | — |
| 46 | 99/50 | 75/200 | — | 95/100 | 80/25 | 0/100 | 100/200 |
| 47 | 70/12 | 0/50 | — | 90/100 | — | — | 90/50 |
| 48 | — | — | — | 0/100 | — | — | — |
| 49 | 99/50 | 50/12 | — | 80/100 | — | — | 75/200 |
| 50 | 85/50 | 0/200 | — | 80/100 | — | — | 75/200 |
| 51 | 85/50 | 0/200 | 90/25 | 80/100 | 0/100 | 0/=100 | 90/200 |
| 52 | 70/50 | 0/200 | 0/100 | 80/100 | 0/100 | 0/100 | 90/200 |
| 53 | — | — | 0/100 | 0/100 | 0/100 | 0/100 | — |
| 54 | — | — | 0/100 | 85/100 | 0/100 | 0/100 | — |
| 55 | 70/12 | 0/200 | 0/100 | 95/100 | 0/100 | 50/100 | 90/200 |
| 56 | 50/12 | 0/200 | 80/50 | 80/200 | 0/200 | 0/200 | 75/200 |
| 57 | 70/50 | 75/200 | 0/200 | 90/200 | 25/200 | 50/12 | 90/200 |
| 58 | — | — | 50/200 | 0/200 | 0/200 | 0/200 | — |
| 59 | 70/50 | 0/200 | 50/50 | 80/200 | 0/200 | 0/200 | 50/200 |
| 60 | — | 50/200 | 0/200 | 95/200 | 25/200 | 0/200 | — |
| 61 | — | 0/200 | 0/200 | 0/200 | 0/200 | 0/200 | — |
| 62 | — | 0/200 | 0/200 | 90/200 | 0/100 | 50/12 | — |
| 63 | — | 0/200 | 0/200 | 100/200 | 0/200 | 0/200 | — |
| 64 | — | 0/200 | 0/200 | 80/200 | 0/200 | 0/200 | — |
| 65 | — | 0/200 | 0/200 | 95/200 | 0/200 | 0/200 | — |
| 66 | — | 50/50 | 0/200 | 90/200 | 0/200 | 0/200 | — |
| 67 | — | 0/200 | 0/200 | 95/200 | 0/200 | 0/200 | — |
| 68 | 70/12 | 80/50 | 0/200 | 90/200 | 0/200 | 0/200 | 90/200 |
| 69 | 85/50 | 80/200 | 0/200 | 100/200 | 0/200 | 0/200 | 75/200 |
| 70 | — | 50/200 | 0/200 | 0/200 | 0/200 | 0/200 | — |
| 71 | — | 0/200 | 0/200 | 100/200 | 0/200 | 50/12 | — |
| 72 | — | 0/200 | 50/200 | 90/200 | 0/200 | 0/200 | — |
| 73 | — | 0/200 | 0/200 | 0/200 | 25/200 | 0/200 | — |
| 74 | — | 0/200 | 0/200 | 0/200 | 0/200 | 0/200 | — |
| 75 | 0/200 | 50/200 | 0/12 | 90/50 | 50/200 | 0/200 | — |
| 76 | — | 0/200 | 0/200 | 0/200 | 0/200 | 0/200 | — |
| 77 | 85/200 | 90/200 | 0/200 | 90/200 | 80/200 | 0/200 | — |
| 78 | — | 0/200 | 0/200 | 0/200 | 0/200 | 0/200 | — |
| 79 | — | 0/200 | 0/200 | 100/200 | 0/200 | 0/200 | — |
| 80 | 85/50 | 50/200 | 50/200 | 100/200 | 0/200 | 0/200 | 75/200 |
| 81 | 0/200 | 75/200 | 0/200 | 100/200 | 25/50 | 85/50 | — |
| 82 | 0/200 | 90/200 | 0/200 | 0/200 | 50/50 | 0/200 | 50/100 |
| 83 | 95/200 | 50/200 | 0/200 | 90/200 | 50/200 | 0/200 | — |
| 84 | 0/200 | 0/200 | 0/200 | 90/200 | 50/200 | 0/200 | — |
| 85 | 70/200 | 90/200 | 0/200 | 90/200 | 80/200 | 0/200 | — |
| 86 | 85/200 | 0/200 | 0/200 | 90/200 | 50/200 | 0/200 | 0/100 |
| 87 | 100/200 | 95/200 | 0/200 | 90/200 | 80/200 | 50/12 | 50/10 |
| 88 | 70/200 | 90/200 | — | 90/200 | 80/50 | 0/200 | 0/100 |
| 89 | 70/200 | 95/200 | 0/200 | 90/200 | 90/200 | 0/200 | 80/100 |
| 90 | 85/200 | 0/200 | 0/200 | 0/200 | 0/200 | 0/50 | — |
| 91 | 70/200 | 70/200 | 0/200 | 80/200 | 25/200 | 85/12 | — |
| 92 | 85/200 | 70/200 | 0/200 | 90/200 | 50/50 | 50/50 | — |
| 93 | 99/200 | 90/50 | 0/200 | 90/200 | 50/200 | 75/200 | 50/100 |
| 94 | 70/200 | 90/200 | 0/200 | 80/200 | 50/200 | 85/200 | — |
| 95 | 95/200 | 70/50 | 0/200 | 80/200 | 50/200 | 0/200 | — |
| 96 | 95/200 | 95/200 | 50/200 | 0/200 | 0/50 | 75/200 | 0/100 |
| 97 | 0/50 | 70/200 | 0/200 | 80/200 | 0/200 | 50/12 | — |
| 98 | 50/200 | 99/200 | 0/200 | 90/200 | 50/200 | 0/50 | 0/100 |
| 99 | 50/200 | 75/200 | — | 0/200 | 0/200 | 50/200 | — |
| 100 | 50/200 | 0/200 | — | 0/200 | 0/200 | 50/200 | — |
| 101 | 50/200 | 75/200 | — | 0/200 | 0/200 | 0/200 | — |
| 102 | 50/200 | 50/200 | — | 0/200 | 0/200 | 0/200 | — |
| 103 | 50/200 | 50/200 | — | 0/200 | 0/200 | 85/200 | — |
| 104 | 0/200 | 50/200 | — | 0/200 | 0/200 | 0/200 | — |
| 105 | 90/200 | — | — | 0/200 | 0/200 | 0/200 | — |
| 106 | 50/200 | 0/200 | — | 0/200 | 0/200 | 0/200 | — |
| 107 | 0/200 | 0/200 | — | 0/200 | 0/200 | 50/200 | — |
| 108 | 90/200 | 0/200 | — | 90/200 | 0/200 | 0/200 | — |
| 109 | 50/200 | 0/200 | — | 0/200 | 0/200 | 0/200 | — |
| 110 | 70/200 | 75/200 | — | 90/200 | 0/200 | 0/200 | — |
| 111 | 85/200 | 0/200 | — | 80/200 | 0/200 | 0/200 | — |
| 112 | 99/200 | 0/200 | — | 90/100 | 50/200 | 0/200 | 50/100 |
| 113 | 50/200 | 0/200 | — | 0/200 | 25/50 | 0/200 | — |
| 114 | 95/200 | 0/200 | — | 90/200 | 0/200 | 0/200 | 50/100 |
| 115 | — | — | — | 0/200 | — | — | — |
| 116 | 0/200 | 50/12 | — | 0/200 | 0/200 | 0/200 | — |
| 117 | 95/50 | 0/200 | — | 0/200 | 0/200 | 0/200 | — |
| 118 | 100/200 | 75/200 | — | 90/200 | 0/200 | 0/200 | — |

TABLE 5-continued

| Compound | % Control* versus Assorted Fungi | | | | | | |
|---|---|---|---|---|---|---|---|
| | CDM | RB | RSB | TLB | WLR | WPM | WSR |
| 119 | 70/200 | 50/200 | — | 80/200 | 0/200 | 0/200 | — |
| 120 | 90/200 | 0/200 | — | 80/50 | 0/200 | 0/200 | — |

*Values given as % Control/Ppm application rate

TABLE 6

EC 50 Values of Selected Compounds Against Pythium ultimum

| Compound | EC50, ppm |
|---|---|
| 7 | 50 |
| 42 | 9 |
| 43 | 5.2 |
| 48 | 8.2 |
| 53 | 10.2 |
| 61 | 59.5 |
| 70 | 5.0 |
| 73 | 8.4 |
| 74 | 5 |
| 76 | 13.2 |
| 78 | 23.9 |
| 113 | 6.9 |
| 116 | 10.3 |

While the invention has been described in sufficient detail for those skilled in the art to be able to make and use it, various alternatives, modifications, and improvements should become apparent from the forgoing disclosure without departing from the spirit and scope of the invention.

We claim:

1. A compound of the formula

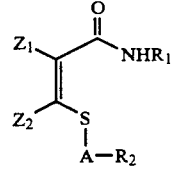

wherein $R_1$ is -n-octyl, $Z_1$ is hydrogen, $Z_2$ is hydrogen, $R_2$ is ethyl, and A is carbonyl.

2. A compound of the formula

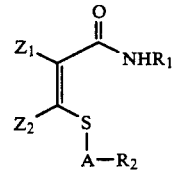

wherein $R_1$ is selected from a group consisting of 2,4,4-trimethyl-2-pentyl and propargyl; $Z_1$ is hydrogen, $Z_2$ is hydrogen, $R_2$ is phenyl, and A is carbonyl.

* * * * *